United States Patent [19]
Kikuchi et al.

[11] Patent Number: 6,114,601
[45] Date of Patent: Sep. 5, 2000

[54] PLANT GENES ENCODING FLAVONOID-3', 5'-HYDROXYLASE

[75] Inventors: Yasuhiro Kikuchi, Tsukuba; Shigeto Kiyokawa, Aomori; Yukihisa Shimada, Tokyo; Masaya Ohbayashi, Tsukuba; Ritsuko Shimada, Tokyo; Yasushi Okinaka, Sapporo, all of Japan

[73] Assignee: Kyowa Hakko Kogyo Co., Ltd., Tokyo, Japan

[21] Appl. No.: 08/606,505

[22] Filed: Feb. 23, 1996

Related U.S. Application Data

[63] Continuation of application No. 08/295,746, filed as application No. PCT/JP92/01520, Nov. 20, 1992, abandoned.

[30] Foreign Application Priority Data

Mar. 2, 1992 [JP] Japan ................................. 4-044963

[51] Int. Cl.$^7$ ......................... C12N 15/29; C12N 15/55; C12N 15/82; A01H 5/00
[52] U.S. Cl. ...................... 800/282; 800/317.3; 800/323; 800/323.1; 800/323.3; 435/69.1; 435/195; 435/320.1; 435/414; 435/419; 435/468; 536/23.2; 536/23.6
[58] Field of Search ................................. 536/23.2, 23.6; 435/69.1, 70.1, 172.3, 195, 320.1, 419, 468, 414; 47/58; 800/205, DIG. 10, 36, 40, 43, 260, 282, 317.3, 323, 323.1, 323.3

[56] References Cited

U.S. PATENT DOCUMENTS 5,349,125  9/1994  Holton et al. .......................... 800/205

FOREIGN PATENT DOCUMENTS

| 0154186 | 9/1985 | European Pat. Off. . |
|---------|--------|----------------------|
| 0173378 | 3/1986 | European Pat. Off. . |
| 0522880 | 1/1993 | European Pat. Off. . |
| 2305    | 1/1990 | Japan . |
| 184370  | 7/1993 | Japan . |
| WO 06744 | 11/1986 | WIPO . |
| WO 12084 | 10/1990 | WIPO . |
| WO 20206 | 10/1993 | WIPO . |

OTHER PUBLICATIONS

Nucleic Acids Research, vol. 14, No. 16 (1986) 6773–6774. Jaiswal et al.
Journal of Biological Chemistry, vol. 264, No. 24 (1989) 14129–14135. Nixon et al.
Plant Breeding, vol. 106 (1991) 1–26. Forkman, G.
Proc. Natl. Acad. Sci., vol. 87 (May 1990) 3904–3908. Bozak et al.
Proc. Natl. Acad. Sci., vol. 86 (Mar. 1989) 1934–1938. Gould et al.
Biochem. and Biophys. Res. Comm., vol. 167, No. 2 (1990) 504–506. Kalman et al.
Zeitschrift fur Naturforschung, vol. 37c (1982) 19–23. Stotz et al.
Mol. App. to Crop Improv., vol. 7 (127–141). 1991. Dennis et al., eds.
Proc. Natl. Acad. Sci., vol. 86, (1989) 1465–1469. Feyereisen et al.
Methods in Enzymology, vol. 206 (1991) 149–166. Spurr et al.
Mol. Pharmacol., vol. 40, No. 3 (1991) 375–382. Furuya et al.
Plant Molecular Biology, vol. 13, (1989) 287–294. Mol et al.
Nature, vol. 330 (1987) 677–678. Meyer et al.
Nature, vol. 333 (1988) 866–869. Van der Krol et al.
The Plant Cell, vol. 2 (1990) 279–289. Napoli et al.
The Plant Cell, vol. 2 (1990) 291–299. van der Krol et al.
Petunia, Springer Verlag (Berlin) (1984) 49–76. Wiering et al., Sink, K.C. (ed.).
Nikkei Biotech, Nikkei Business Publications, Inc., vol. 238 (1991) 1–2.
Saito et al. 1991. Proc. Natl. Acad. Sci. USA 88(16): 7041–7045.
van Turen et al. 1988. EMBO J. 7(5): 1257–1263.
The Plant Cell, vol. 3, Jan. 1991, pp. 39–48, van Turen et al.
The Flavonoids (Harborne, J.B., ed. Chapman and Hall, London) 399–425. (1988). Heller et al.
Stevenson, T.W. (Dennis et al., eds).
Molecular Approaches to Crop Improvement, Springer Verlag N.Y. (1991) 127–148.
J. Biol. Chem., vol. 266 (1991) 13469–72. Porter et al.
Pharmacol. Rev., vol. 40 (1988) 243–288. Gonzalez, F. J.
Plant Physiol., vol. 96 (1991) 669–674. Donaldson et al.
Proc. Natl. Acad. Sci. USA, vol. 87 (1990) 3904–08. Bozak et al.
Proc. Natl. Acad. Sci. USA, vol. 85 (1988) 7221–25. Kalb et al.
Z. Naturforschung, vol. 37c (1982) 19–23.

*Primary Examiner*—David T. Fox
*Attorney, Agent, or Firm*—Fitzpatrick, Cella, Harper & Scinto

[57] ABSTRACT

The present invention relates to a DNA which encodes a polypeptide having flavonoid-3',5'-hydroxylase activity, a recombinant DNA containing said DNA, and a plant having a pigment pattern which the plant does not originally have and which is acquired by transformation with said recombinant DNA.

8 Claims, 1 Drawing Sheet

Pro-Phe-Gly-( )-Gly-( )-Arg-( )-Cys-Ile-Gly
       -Ser-                    -Leu-
                                   -Val-
                                   -Ala-
                                   -Pro-

Sense primer                    Antisense primer

※    ( ) may be any amino acid.

6,114,601

PLANT GENES ENCODING FLAVONOID-3', 5'-HYDROXYLASE

This application is a continuation of application Ser. No. 08/295,746, filed Aug. 30, 1994, now abandoned, which is a 371 of PCT/JP92/01520 filed Nov. 20, 1992.

TECHNICAL FIELD

The present invention relates to a technique to breed plants or plant cells using recombinant DNA technology. More particularly, the present invention relates to a technique to breed novel plant cells or novel plants which show exogenous pigment patterns by transforming plant cells or plants with a recombinant DNA containing a DNA which encodes a polypeptide having flavonoid-3',5'-hydroxylase activity (hereinafter also referred to as the DNA encoding flavonoid-3',5'-hydroxylase).

BACKGROUND ART

Crossing between varieties has been conventionally employed as a method for altering the color of flowers and fruits of plants. However, crossing is carried out between varieties of the same genus, and usually of the same species, and therefore, it is extremely difficult to give specific colors to certain plant species. For example, in spite of longtime efforts of breeders, no one has yet successfully bred a blue rose or a blue carnation.

In recent years, recombinant DNA technology has enabled plant breeding between different species or genus, and it is expected to breed new plants having unprecedented pigment patterns which can not be obtained by the conventional breeding methods by crossing (Plant Molecular Biology, vol.13, p.287–294, 1989). For example, it is reported that petunia showing unprecedented brick-red color on flowers was bred by cloning a gene encoding dihydroflavonol-4-reductase, which is an enzyme participating in pigment biosynthetic pathway, from maize and introducing it into petunia (Japanese Published Unexamined Patent Application No. 2305/90; Nature, vol.330, p.677–678, 1987). Further, a report has been made of a case in which new pigment patterns were produced by introducing the chalcone synthase gene of petunia at the sense or anti-sense orientation to partially inhibit the expression of the gene (Nature, vol.333, p.866–869, 1988; The Plant Cell, vol.2, p.279–289, 1990; The Plant Cell, vol.2, p.291–299, 1990).

Biosynthetic pathways for anthocyanins, which contribute to blue or red color of flowers, have been studied genetically and biochemically in detail using petunia and others (Petunia, Edited by K. C. Sink, Springer Verlag, p.49–76, 1984; The Flavonoids, Edited by J. B. Harborne, Chapman and Hall, p.399–425, 1988; Molecular Approaches to Crop Improvement, Edited by E. S. Denis and D. J. Rewerin, Springer Verlag, p.127–148, 1991). As a result of these studies, it is shown that the presence/absence of hydroxyl group at the 3'- and 5'-positions of the B ring of anthocyanin greatly affects the color of flowers, and also it is shown that, generally, the blue color of flowers is intensified as the B ring is hydroxylated in a higher degree. The hydroxylation of the B ring of anthocyanins occurs at the stage of their precursors, flavanones or dihydroflavonols. As enzymes which catalyze this hydroxylation, two types of enzyme have been known; flavonoid-3'-hydroxylase which hydroxylates only the 3'-position of the B ring, and flavonoid-3',5'-hydroxylase which hydroxylates both the 3'- and 5'-positions. Petunia with blue flowers has both the enzymes, but that with red flowers has only the former one. Plants like roses, carnations, and chrysanthemums do not have anthocyanins which have B ring hydroxylated at both the 3'- and 5'-positions, and therefore are considered not to have the latter type of enzyme.

These hydroxylases are localized in the microsomal membrane and require NADPH as a coenzyme. They are presumed to be members of the cytochrome P450 enzyme group on the basis of their behavior against various inhibitors (The Flavonoids, Edited by J. B. Harborne, Chapman and Hall, p.399–425, 1988; Molecular Approaches to Crop Improvement, Edited by E. S. Denis and D. J. Rewerin, Springer Verlag, p.127–148, 1991).

Cytochrome P450 is an enzyme group which is widely distributed among eucaryotes and procaryotes and which is involved in the biosynthesis of important lipids such as steroids and in the oxidative metabolism of lipophilic substances. In higher animals, it forms a super family consisting of one hundred or more molecular species (J. Biol. Chem., vol.266, p.13469–13472, 1991; Pharmacol. Rev., vol.40, p.243–288, 1988). In plants, cinnamic acid-4-hydroxylase and kaurene oxidase are considered to belong to the cytochrome P450 group (Plant Physiol., vol.96, p.669–674, 1991). Further, a gene encoding a cytochrome P450 enzyme whose function is unknown has been cloned from avocado (Proc. Natl. Acad. Sci. USA, vol.87, p.3904–3908, 1990). As a result of the comparison of the amino acid sequences of various types of cytochrome P450 enzymes, it is known that the sequence of the heme-binding site is conserved (Proc. Natl. Acad. Sci. USA, vol.85, p.7221–7225, 1988; Pharmacol. Rev. vol.40, p.243–288, 1988).

In petunia, flavonoid-3',5'-hydroxylase is encoded by two dominant genes called Hf-1 and Hf-2. The enzymes encoded by the genes are isozymes, and the degree of expression of Hf-1 is higher (Petunia, Edited by K. C. Sink, Springer Verlag, p.49–76, 1984). Further, characteristics of said enzyme of Verbena have been reported (Z. Naturforschung, vol.37c, p.19–23, 1982).

It is also reported that 3',5'-hydroxylase, a key enzyme in the biosynthesis of delphinidin, which is a blue pigment in petunia, has been successfully cloned (Nikkei Biotech, Aug. 26, 1991). However, no report has been made yet of a case in which the cloned gene of said enzyme is allowed to express in a plant to alter pigments in the plant.

SUMMARY OF THE INVENTION

The present invention provides a DNA which encodes a polypeptide having flavonoid-3',5'-hydroxylase activity which is represented by the amino acid sequence shown by SEQ ID NO: 1, 63 or 64, a DNA which hybridizes with said DNA, a recombinant DNA constructed by incorporating any of these DNAs or a part of their sequences into a vector DNA, and plant cells or plants which carry said recombinant DNA.

It is possible to breed plants having novel pigment patterns by introducing said DNA, i.e., a DNA that encodes a polypeptide having flavonoid-3',5'-hydroxylase activity, into plant cells or plants by the use of recombinant DNA technology.

The DNA of the present invention may be any DNA which encodes a polypeptide having flavonoid-3',5'-hydroxylase activity, i.e., a DNA which encodes a polypeptide represented by the amino acid sequence shown by SEQ ID NO: 1, 63 or 64, or a DNA which hybridizes with said DNA (hereinafter referred to as hDNA). The hDNA may be any DNA which hybridizes with the DNA encoding the polypeptide represented by the amino acid sequence shown by SEQ ID NO: 1, 63 or 64 in 2×SSC (0.3 M sodium chloride, 0.03 M sodium citrate, pH 7.0) at 50° C.

The DNA which encodes the polypeptide represented by the amino acid sequence shown by SEQ ID NO: 63 or 64 hybridizes with the DNA which encodes the polypeptide represented by the amino acid sequence shown by SEQ ID NO: 1 under the above-mentioned conditions.

Other examples of the DNAs of the present invention include DNAs wherein a part of the nucleotide sequence of the above-mentioned DNAs is deleted or replaced with other nucleotide sequences, as far as such DNAs encode a polypeptide having flavonoid-3',5'-hydroxylase activity.

Examples of the DNA sources include a genomic DNA of plants which have flavonoid-3',5'-hydroxylase, and a cDNA which is synthesized from an mRNA extracted from the expression sites of said enzyme using a reverse transcriptase. Examples of the plants having said enzyme include petunia (Solanaceae), pansy (Violaceae), primrose (Primulaceae), delphinium (Ranunculaceae), sweet pea (Leguminosae), Japanese gentian (Gentianaceae), balloon flower (Campanulaceae), forget-me-not (Boraginaceae), hydrangea (Saxifragaceae), verbena (Verbenaceae), dayflower (Commelinaceae), iris (Iridaceae), hyacinth (Liliaceae), Russell prairie gentian (Gentianaceae), and campanula (Campanulaceae).

In the present invention, on the basis of the presumption that flavonoid-3',5'-hydroxylase is a member of the cytochrome P450 family, DNA sequences encoding the amino acid sequence of the heme-binding site of cytochrome P450 (hereinafter referred to as the core sequence) are amplified and isolated using the PCR method.

The core sequence is the region that shows high homology among different molecular species of cytochrome P450 and among those of different organisms. More than 80% of the sequences for cytochrome P450 which have been ever isolated have the core sequence shown in FIG. 1 (DNASIS™ Data Base CD, 009-1 and 2, Hitachi Software Engineering Co., Ltd., 1990). DNA sequences which can encode the amino acid sequence of the region indicated by arrows are hypothesized. Then, in order to amplify and isolate the DNA sequences encoding this region by the PCR method, 16 types of sense primers shown by SEQ ID NO: 2 to 17, and 12 types of antisense primers shown by SEQ ID NO: 18 to 29 are chemically synthesized. The sense primers are synthetic oligonucleotides each consisting of 18 bases. Each sense primer has, at the 3' end side, one of the 16 types of 8-base DNA sequences encoding Pro-Phe-Gly or Pro-Phe-Ser and lacking the DNA base that corresponds to the third base of the codon for Gly or Ser. The sense primer has a 10-base sequence containing a recognition site for a restriction enzyme, EcoRI, at the 5' end side. The antisense primers are synthetic oligonucleotides each consisting of 18 bases. Each antisense primer has, at the 3' end side, a complementary DNA sequence for one of the 12 types of 8-base DNA sequences encoding Cys-Xxx-Gly wherein Xxx represents either Ile, Met, Leu, Phe, Val, Ala, or Pro, and lacking the DNA base that corresponds to the third base of the codon for Gly. The DNA base corresponding to the third base of the codon for Xxx may be any one of A, C, G and T represented by N. The antisense primer has a 10-base sequence containing a recognition site for a restriction enzyme, BamHI, at the 5' end side.

By the use of PCR in which these synthetic DNA primers are employed in combination, various DNA fragments which encode the core sequence can be amplified and isolated, and their DNA sequences can be determined. As cytochrome P450 forms a super family which consists of various molecular species, it is expected that various types of core sequences can be obtained from one template DNA. During the process of the present invention, 15 types of core sequences shown by SEQ ID NO: 30 to 44 were obtained.

It is necessary to make a presumption as to which core sequence is the target sequence among the thus obtained core sequences. In the present invention, the target sequence is presumed by investigating whether the expression/non-expression of each core sequence is genetically linked to the presence/absence of said enzyme activity. In order to investigate the genetic linkage, a petunia which originally has said enzyme (a blue flower cultivar) is backcrossed with a mutant petunia variety which lacks said enzyme (a red flower cultivar) to produce a genetically segregating population (1:1) regarding the presence/absence of said enzyme. Then, the mode of expression of each core sequence in the petals of individual plants in this population is investigated. If the mode of expression of any core sequence agrees with (is genetically linked with) the presence/absence of said enzyme, the core sequence is presumed to be a part of the gene encoding said enzyme.

In order to investigate whether a core sequence is expressed in the petals, the present invention uses a method called SSP (single specific primer)·polymerase chain reaction (PCR)SSP·PCR is a method described in Biochemistry Biophysics Research Communication, vol.167, p.504–506, 1990. By the use of this method, it is possible to amplify a DNA sequence flanking a core sequence and to determine the presence/absence of the corresponding product. First, specific DNA primers are synthesized based on the DNA sequences encoding the core sequences. In the present invention, 15 types of DNAs (K primers 01 to 15) shown by SEQ ID NO: 45 to 59 were synthesized and used as the specific DNA primers. Then, cDNAs are prepared from the petals of each petunia plant in the backcrossed population, digested with appropriate restriction enzymes, and then ligated with appropriate double-strand synthetic DNA (called cassette) which had the corresponding cleaved ends using a ligase to prepare templates. In the present invention, synthetic DNAs shown by SEQ ID NO: 60 and 61 were annealed and used as the cassette. The synthetic DNA shown by SEQ ID NO: 60 was also used as the primer for the cassette. With the template DNA ligated to the cassette, PCR was carried out between the specific primer and the primer for the cassette, whereby the DNA sequence flanking the core sequence is amplified. The presence/absence of its product reflects the expression/non-expression of the core sequence.

As a result of the search in the petunia population obtained by the backcrossing, it was revealed that the presence/absence of a product (approximately 85 bp) which was amplified by SSP·PCR using the specific primer (K14) shown by SEQ ID NO: 58 was completely linked with the presence/absence of said enzyme activity. As this primer was designed based on the core sequence shown by SEQ ID NO: 43, this sequence is assumed to be the core sequence of said enzyme. On the basis of SEQ ID NO: 43, the primer (J14) shown by SEQ ID NO: 62 was synthesized and SSP·PCR was carried out. As a result, the presence/absence of a product of approximately 280 bp was completely linked with the presence/absence of the enzyme activity. This result strongly suggests that the core sequence shown by SEQ ID NO: 43 is the target sequence.

The product of approximately 280 bp thus amplified is assumed to be a part of the cDNA sequence that encodes said enzyme. The full length cDNA sequence shown by SEQ ID NO: 1 can be obtained by preparing petunia flower cDNA library according to the method described in a book by Maniatis et al., and then searching the library using the above-mentioned product as a probe. If the expression of the obtained sequence in a plant which originally does not have said enzyme results in the detection of said enzyme activity in the plant, it will be proved that this sequence is the DNA sequence encoding the polypeptide having said enzyme activity. In the present invention, the DNA shown by SEQ ID NO: 1 was introduced into tobacco and petunia cultivars both of which do not have said enzyme, and expressed. As a result, said enzyme activity was detected in both plants, and thus the DNA was proved to be the DNA encoding the polypeptide having said enzyme activity.

Cloning of DNAs can be carried out using a material such as a cDNA which is synthesized based on an mRNA extracted from the petals of petunia using a reverse transcriptase.

DNA cloning and DNA analysis can be carried out according to general techniques described in Molecular Cloning a Laboratory Manual Second Edition, J. Sambrook, E. F. Frisch, T. Maniatis, Cold Spring Harbor Laboratory Press, 1989 (hereinafter referred to as the book by Maniatis et al.), and the like.

PCR can be carried out according to ordinary techniques described in PCR Technology, Edited by H. A. Ehrlich, Stockton Press, 1989, PCR Protocols, Edited by M. A. Innis, D. H. Gerfand, J. J. Sninsky, and T. J. White, Academic Press, 1990, and the like.

Determination of nucleotide sequences can be carried out according to methods using the Taq Dideoxy™ Terminator Cycle Sequencing Kit (ABI Co., Ltd.) and the Model 373A DNA Sequencing System (ABI Co., Ltd.), and the like.

DNA fragments encoding polypeptides which have analogous sequences and said enzyme activity can be cloned from any of the plants mentioned above as the DNA source by an ordinary method using, as a probe for hybridization, the whole or a part of the DNA sequence shown by SEQ ID NO: 1 which encodes the polypeptide having said enzyme activity and is derived from petunia as above.

In the present invention, according to the above-mentioned method, a DNA which encodes a polypeptide having the amino acid sequence shown by SEQ ID NO: 63 has been cloned from Russell prairie gentian, and a DNA which encodes a polypeptide having the amino acid sequence shown by SEQ ID NO: 64 has been cloned from campanula.

New coloration can be introduced into a host plant which does not have said enzyme by introducing a DNA fragment which encodes a polypeptide having said enzyme activity into the host plant, allowing it to express, and thereby hydroxylating the 3'- and 5'-positions of anthocyanin pigments. Examples of such host plants include rose (Rosaceae), carnation (Caryophyllaceae), petunia (Solanaceae), tobacco (Solanaceae), chrysanthemum (Compositae), stock (Cruciferae), begonia (Begoniaceae), snapdragon (Scrophulariaceae), camellia (Theaceae), lily (Liliaceae), and orchid (Orchidaceae).

Further, in plant species which originally have said enzyme, the enzyme activity can be inhibited by introducing said DNA fragment at the antisense or sense orientation and allowing it to express (Nature, vol.333, p.866–869, 1988; The Plant Cell, vol.2, p.279–289, 1990; The Plant Cell, vol.2, p.291–299, 1990). By application of such methods, breeding of a plant species having an unprecedented pigment pattern can be achieved.

In order to introduce the DNA fragment which encodes the polypeptide having said enzyme activity into plants and allow it to express, it is necessary to introduce an appropriate promoter at the site upstream of the region encoding the polypeptide having said enzyme activity. An example of a promoter that works in plants is 35 S promoter of Cauliflower Mosaic Virus (CaMV) (Cell, vol.21, p.285–294, 1980). An example of a promoter that acts site-specifically is the promoter of petunia chalcone synthase (CHS) gene which works strongly only in the petals (Plant Molecular Biology, vol.15, p.95–109, 1990). The above-mentioned DNA fragment can be expressed in plants by ligating such a promoter. When a DNA which encodes the polypeptide having said enzyme activity is cloned from the genomic DNA, it may have been linked with an inherent promoter, and in such cases, there is no need to further link it with another promoter.

Further, efficient expression can be expected by introducing a terminator for the termination of transcription at the site downstream of the region encoding the polypeptide having said enzyme activity (EMBO Journal, vol.7, p.791–799, 1988).

In order to select plant cells or plants in which the DNA has been introduced, it is preferable to introduce an appropriate marker into the DNA. Examples of such markers include the kanamycin resistance gene and the hygromycin resistance gene (Plant Molecular Biology, vol.5, p.299–302, 1985). When a microorganism belonging to the genus Agrobacterium is used to introduce the DNA into plant cells or plants, it is necessary to attach the border sequences derived from Ti plasmid at both ends of the sequence to be inserted into plant chromosomes (Nature, vol.313, p.191–196, 1985). Further, it is necessary to link the insert sequence with a sequence that allows stable retention of plasmids in a cell of a microorganism belonging to the genus Agrobacterium. An example of an expression vector for plants which meets the above-mentioned requirements is pBI121 (Clonetech Co., Ltd.).

Examples of methods for introducing said DNA fragment inserted in a vector as described above into plants and obtaining genetically stable transformed plants include: 1) a method for dicotyledons in which the DNA is introduced via *Agrobacterium tumefaciens*, the bacterium causing crown gall disease (Methods in Enzymology, vol.118, p.627–640, 1986); 2) a method in which the DNA is pelted in conjunction with microparticles of substances such as gold and tungsten at plant cells at a high speed to be incorporated into cell nuclei and then into chromosomes (the high-speed microparticle method; Plant Molecular Biology, vol.11, p.433–439, 1989; Bio/Technology, vol.9, p.1080–1085, 1991); and 3) a method in which the DNA is introduced in conjunction with calcium chloride and polyethylene glycol into protoplasts which have been prepared with cell wall-degrading enzymes (Nature, vol.296, p.72–74, 1982; Nature, vol.319, p.791–793, 1986). The method 1) can be efficiently carried out by incorporating the insert DNA into a binary vector such as pBI121 (Nucleic Acids Research, vol.12, p.8711–8721, 1984). According to the method 2), the DNA can be introduced into plants which cannot be infected with a microorganism belonging to the genus Agrobacterium such as monocotyledons. After the introduction of said DNA fragment incorporated into a vector into plant cells according to the methods described above, plant cells in which the introduced DNA is stably retained in the chromosome are selected by utilizing appropriate marker genes such as those for drug resistance. By inducing the differentiation of such plant cells, transformed plants having novel pigment patterns can be obtained.

In the thus obtained transformed plants, the DNA fragments introduced are retained with genetic stability. In other words, said DNA fragments can be maintained semi-persistently through propagation by vegetative reproduction, or by seeds obtained through self-pollination or cross pollination.

Further, it is possible to breed new cultivars which have pigment patterns different from those of the first-generation transformants by crossing the transformants with conventional cultivars to combine their genes.

Thus, a technique is provided which enables the production of unprecedented cultivars having blue or purple flowers by allowing plants having no anthocyanin pigments whose B ring is hydroxylated at both the 3'- and 5'-positions, for example, roses and carnations, to synthesize such pigments.

DETAILED DESCRIPTION OF THE INVENTION

EXAMPLE 1

PCR Amplification and Isolation of the Core Sequences of Cytochrome P450 Genes and Their Sequencing (1) Synthesis of Primers A part of the gene sequence of cytochrome P450 was amplified and isolated by the polymerase chain reaction (PCR) in the following manner. Cytochrome P450 forms a super family consisting of various molecular species, but the similarity in the amino acid sequence among these molecular species is not so high. However, the sequences of the heme-binding region (core sequence) are relatively common.

Figure 1:
FIG. 1 shows the core sequence which is common to more than 80% of the known amino acid sequences for cytochrome P450.
Figure 1:
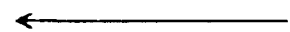

More than 80% of the sequences for cytochrome P450 ever isolated have the core sequence shown in FIG. 1. DNA sequences which could encode the amino acid sequence of the region indicated by arrows were hypothesized. Then, in order to amplify and isolate the DNA sequences encoding this region by the PCR method, primer DNAs were chemically synthesized using the DNA synthesizer, Cyclone Plus™ (manufactured by Milligen/Biosearch). Thus, 16 types of sense primers shown by SEQ ID NO: 2 to 17, and 12 types of antisense primers shown by SEQ ID NO: 18 to 29 were synthesized.

The sense primers are synthetic oligonucleotides each consisting of 18 bases. Each sense primer has, at the 3' end side, one of the 16 types of 8-base DNA sequences encoding Pro-Phe-Gly or Pro-Phe-Ser and lacking the DNA base that corresponds to the third base of the codon for Gly or Ser. The sense primer has a 10-base sequence containing a recognition site for a restriction enzyme, EcoRI, at the 5' end side. The antisense primers are synthetic oligonucleotides each consisting of 18 bases. Each antisense primer has, at the 3' end side, a complementary DNA sequence for one of the 12 types of 8-base DNA sequences encoding Cys-Xxx-Gly wherein Xxx represents either Ile, Met, Leu, Phe, Val, Ala, or Pro, and lacking the DNA base that corresponds to the third base of the codon for Gly. The DNA base corresponding to the third base of the codon for Xxx may be any one of A, C, G and T represented by N. The antisense primer has a 10-base sequence containing a recognition site for a restriction enzyme, BamHI, at the 5' end side.

Each primer was used in a 5 μM aqueous solution.

(2) Extraction of mRNAs from the Petals of Petunia

Extraction of mRNAs from the petals of petunia was carried out according to a modification of the method described in Analytical Biochemistry, vol.163, p.16–20, 1987. That is, petals were cut off from buds of petunia [*Petunia hybrida* cv. Falcon Blue (Sakata Seed Corporation)] which had been grown in a greenhouse. Ten grams (wet weight) of the petals was put into a mortar, frozen by pouring liquid nitrogen, and then ground with a pestle. To the ground petals were added 20 ml of RNA extraction buffer [8 M guanidine hydrochloride, 20 mM Mes buffer (pH 7.0), 20 mM EDTA, 50 mM mercaptoethanol] and then 10 ml of phenol/chloroform/isoamyl alcohol (25:24:1) mixture, and mixed well. The resulting mixture was centrifuged at 10,000×g for 10 minutes, and the upper layer was collected and mixed well with 20 ml of phenol/chloroform/isoamyl alcohol (25:24:1) mixture. The resulting mixture was centrifuged at 10,000×g for 10 minutes, and the upper layer was collected. Then, 14 ml of ethanol and 4 ml of 1 M acetic acid were added to the upper layer, and the mixture was allowed to stand at −70° C. for one hour, followed by centrifugation at 10,000×g for 10 minutes. The precipitate was separated, dissolved in 10 ml of water, and then mixed with 3 ml of 10 M lithium chloride. The resulting mixture was allowed to stand at 4° C. for 2 hours, and centrifuged at 10,000×g for 10 minutes. The precipitate was separated, washed with 10 ml of 70% ethanol, and then dried under vacuum. The dried product was dissolved in 1 ml of elution buffer [10 mM Tris hydrochloride buffer (pH 7.5), 1 mM EDTA, 0.1% sodium dodecyl sulfate (SDS)], and then subjected to purification using 200 μl of oligotex™-dT 30 (Takara Shuzo Co., Ltd.) according to the instructions provided by the manufacturer to give about 3 μg of poly(A) mRNA.

(3) Synthesis of cDNA from Petunia Petal mRNA

A cDNA was synthesized from oligo dT primer using the above-mentioned mRNA as the template and the cDNA Synthesis System Plus RPN1256 (Amersham Co., Ltd.) according to the instructions provided by the manufacturer. About 2 μg of double strand cDNA was obtained.

(4) PCR Amplification of the Consensus Sequence of Cytochrome P450

The above-mentioned cDNA (1 ng) as a template DNA was dissolved in 25 μl of PCR buffer [10 mM Tris hydrochloride buffer (pH 8.3), 1.5 mM magnesium chloride, 25 mM potassium chloride, 0.05% Tween 20, 100 μM dATP, 100 μM dCTP, 100 μM dGTP, 100 μM dTTP]. The solution was put in a 0.5-ml microcentrifugation tube, and as primers, 1 μl of a sense primer (one type) and 1 μl of an antisense primer (one type) both of which were prepared in the step (1) were added thereto. To the mixture was added 0.5 unit of Taq DNA polymerase (Perkin-Elmer Cetus), and 10 μl of mineral oil was layered over the mixture. The reaction was carried out using the DNA Thermal Cycler (Perkin-Elmer Cetus) with the cycle program set as follows; 30 seconds at 93° C. and 1 minute at 37° C. for 3 cycles, followed by 30 seconds at 93° C. and 1 minute at 55° C. for 37 cycles.

PCR was carried out under the above conditions for each of all the 192 combinations of 16 sense primers and 12 antisense primers.

PCR was carried out by reference to PCR Technology, edited by H. A. Ehrlich, Stockton Press, 1989, and PCR Protocols, edited by M. A. Innis, D. H. Gerfand, J. J. Sninsky, and T. J. White, Academic Press, 1990.

(5) Cloning of PCR Products

The products of the above reaction were subjected to 10% polyacrylamide gel electrophoresis and stained with ethidium bromide according to the method described in the book by Maniatis et al. As a result, a DNA band of approximately 50 bp was detected for 23 among the 192 combinations of sense primers and antisense primers. Portions containing the DNA band were cut out from the gel, and DNAs were extracted and purified according to the methods described in the book by Maniatis et al. Each of the obtained DNAs was dissolved in 50 µl of H buffer [50 mM Tris hydrochloride buffer (pH 7.5), 10 mM magnesium chloride, 1 mM dithiothreitol, 100 mM sodium chloride]. To the solution were added 10 units of the restriction enzyme BamHI (Takara Shuzo Co., Ltd.) and 10 units of the restriction enzyme EcoRI (Takara Shuzo Co., Ltd.), and the reaction was carried out at 37° C. for 3 hours. After addition of 150 µl of ethanol, the reaction mixture was allowed to stand at −80° C. for 10 minutes, and then centrifuged at 10,000×g for 10 minutes. The obtained precipitate was washed with 200 µl of 70% ethanol and dried under vacuum. The obtained DNA was dissolved in 10 µl of TE buffer [10 mM Tris hydrochloride buffer (pH 7.5), 1 mM EDTA].

The plasmid vector pUC19 (Takara Shuzo Co., Ltd.) (5 µg) was dissolved in 50 µl of H buffer, and 10 units of the restriction enzyme BamHI (Takara Shuzo Co., Ltd.) and 10 units of the restriction enzyme EcoRI (Takara Shuzo Co., Ltd.) were added. The reaction was carried out at 37° C. for 3 hours. After addition of 150 µl of ethanol, the reaction mixture was allowed to stand at −80° C. for 10 minutes, and then centrifuged at 10,000×g for 10 minutes. The obtained precipitate was washed with 200 µl of 70% ethanol and dried under vacuum. The obtained vector DNA was dissolved in 100 µl of TE buffer.

The vector solution thus prepared (1 µl) was mixed with the solution containing the DNA fragment of approximately 50 bp (10 µl) prepared above, and subjected to ligation at 16° C. for 30 minutes using the DNA Ligation Kit (Takara Shuzo Co., Ltd.) according to the instructions provided by the manufacturer. The volume of the reaction mixture was 60 µl. Highly competent cells of *E. coli* JM109 (Toyobo Co., Ltd.) were transformed with 2 µl of the reaction mixture according to the instructions provided by the manufacturer. According to the method described in the book by Maniatis et al., the cells were cultured at 37° C. for 20 hours on X-gal ampicillin LB agar medium [1% Bacto Tryptone (Difco Laboratories), 0.5% Bacto Yeast Extract (Difco Laboratories), 1% sodium chloride, 40 µg/ml X-gal, 40 µg/ml isopropyl-1-thio-β-D-galactopyranoside (IPTG), 100 µg/ml ampicillin, 1.5% Bacto Agar (Difco Laboratories)]. One of the formed white colonies was isolated and cultured, and plasmid DNA was extracted from the culture and purified.

(6) Determination of DNA Sequences of PCR Products

The nucleotide sequence of the insert fragment in each of the 108 clones prepared as described above were determined using the Taq Dideoxy™ Terminator Cycle Sequencing Kit (ABI) and the Model 373A DNA Sequencing System (ABI) according to the instructions provided by the manufacturer. As a result, 15 types of core sequences shown by SEQ ID NO: 30 to 44 were determined for the cytochrome P450 genes.

EXAMPLE 2

Production of Petunia Backcrossed Population
(1) Analysis of Pigments in the Petals Pigments in the petals were analyzed after converting anthocyanins into anthocyanidins according to the method described in Phytochemical Methods, Second Edition, edited by J. B. Harbone, p.64, Chapman and Hall, 1989. That is, 0.1 to 0.5 g of the petals was cut off and 1 ml of 2N hydrochloric acid was added. The mixture was heated at 95° C. for 40 minutes, and then brought to room temperature. After addition of 300 µl of ethyl acetate followed by thorough mixing, the mixture was allowed to stand still, and the upper ethyl acetate layer was discarded. The residue was heated at 80° C. for 3 minutes to evaporate ethyl acetate, and then brought to room temperature. After addition of 100 µl of isoamyl alcohol followed by thorough mixing, the mixture was allowed to stand still, and the upper isoamyl alcohol layer was collected. Aliquots of 1 to 5 µl of the obtained solution were spotted on a cellulose thin layer plate (Merck & Co., Inc.) and chromatographed using Solvent 1 (conc.hydrochloric acid:acetic acid:water=3:30:10) or Solvent 2 (n-butanol:acetic acid:water=4:1:5) to identify anthocyanidins based on the Rf values and coloration of the pigment spots. Separately, analysis was also carried out using the Hitachi Ion Chromato System (Model L6200 pump and Model L4200 detector), YMC-Pack ODS-A Reversed Phase Column (YMC), and mobile phase consisting of water, acetic acid and methanol (71:10:19) [New High Performance Liquid Chromatography, Application II, p.528, Hirokawa Shoten, 1983]. Anthocyanidins were identified by using commercially available cyanidin, delphinidin, peonidin, and maruvidin (all produced by Extrasynthese) as standards.

(2) Production of Petunia Backcrossed Population

Crossing of petunia was carried out according to the method described in Petunia, edited by K. C. Sink, p.180–202, Springer Verlag, 1984. A blue flower petunia cultivar, Purple Joy (NPI Seeds) was crossed with a red flower petunia cultivar, Falcon Red (Sakata Seed Corporation) to obtain hybrids. The hybrids were backcrossed with Falcon Red, and anthocyanidins in the petals of the obtained hybrids were analyzed. A hybrid plant which had delphinidin as the anthocyanidin component was selected and then backcrossed with Falcon Red. After such backcrossing was repeated four times in total, anthocyanidins in the petals of 18 plants of the obtained hybrid population were analyzed. Among them ten hybrids had delphinidin (delphinidin-type) as anthocyanidin and eight hybrids had cyanidin (cyanidin-type). The color of petals of the former type was grayish purple, and that of the latter was red.

(3) Detection of Flavonoid-3',5'-hydroxylase Activity

Detection of flavonoid-3',5'-hydroxylase activity was carried out according to a modification of the method described in Z. Naturforsch, vol.37c, p.19–23, 1982. That is, 5 g (wet weight) of petals of buds was disrupted using mortar and pestle at 0° C., with 2.5 g of quartz sand (Sigma), 2.5 g of Dow X 1×2 (The Dow Chemical), and 10 ml of buffer for enzyme extraction [0.1 M potassium phosphate buffer (pH 7.5), 20% glycerol, 10 mg/ml sodium ascorbate]. After centrifugation at 12,000×g for 20 minutes, the obtained supernatant (10 ml) was mixed with 0.4 ml of 1 M magnesium chloride. The mixture was allowed to stand at 0° C. for 10 minutes, and centrifuged at 17,000×g for 20 minutes to obtain precipitate. The precipitate was suspended in a small quantity of the buffer for enzyme extraction to make a final volume of 500 µl, and the suspension was used as the microsome fraction.

An aliquot of 100 µl of the microsome fraction was mixed with 400 µl of a reaction mixture [0.1 M potassium phosphate buffer (pH 7.5), 20% glycerol, 10 mg/ml sodium ascorbate, 0.25 mM NADPH (Sigma), 0.25 mM dihydroquercetin (Sigma)], and allowed to react at 25° C. for 30 minutes. After addition of 250 µl of ethyl acetate, the mixture was allowed to stand still, and the upper layer (ethyl acetate layer) was collected, followed by evaporation of ethyl acetate. The residue was dissolved in 10 μl of ethyl acetate, and an aliquot of 5 μl of the solution was spotted on a cellulose thin layer plate (Merck & Co., Inc.) and chromatographed using Solvent 3 (chloroform:acetic acid:water=10:9:1). Flavonoids detected under the UV light were identified based on the Rf values. As a result, it was shown that dihydroquercetin had been converted into dihydromyricetin by the action of flavonoid-3',5'-hydroxylase.

Among the plants of the above-mentioned population obtained by backcrossing, said enzyme activity was detected in the delphinidin-type plants. On the other hand, it was not detected in the cyanidin-type plants. Further, said enzyme activity was detected in Falcon Blue (Sakata Seed Corporation) and Purple Joy (NPI Seeds), which were blue flower petunia cultivars, but was not detected in Falcon Red (Sakata Seed Corporation) and Falcon Salmon (Sakata Seed Corporation), which were red flower petunia cultivars.

EXAMPLE 3

SSP-PCR Using the Core Sequence of Cytochrome P450

(1) Synthesis of K Primers

On the basis of 15 types of the core sequences for cytochrome P450 shown by SEQ ID NO: 30 to 44 which were obtained in Example 1 (6), 15 types of PCR primers shown by SEQ ID NO: 45 to 59 were chemically synthesized using the DNA Synthesizer Cyclone Plus (Milligen/Biosearch). Each primer was used in a 5 μM aqueous solution. The primers were named K01 to K15 primers, respectively, and collectively referred to as K primers. K primers are synthetic DNA primers each having a 17-base sequence which starts from the codon for glycine located at the C-terminus of the amino acid sequence of the core and extends toward the N-terminus, and correspond to the sequences from the 32nd nucleotide to the 16th nucleotide in the core DNA sequences shown by SEQ ID NO: 30 to 44.

(2) Synthesis of a Cassette and a Primer for the Cassette

Oligonucleotides indicated by SEQ ID NO: 60 and 61 were chemically synthesized using the DNA Synthesizer Cyclone Plus (Milligen/Biosearch), and a 20 μM aqueous solution of each oligonucleotide was prepared. After 100 μl each of the solutions were mixed, the mixture was heated at 95° C. for 10 minutes, and then kept at 50° C. for one hour to obtain a double strand DNA, which is called a cassette. One end of the cassette forms a cohesive end of CG-protruding type, and therefore, can be efficiently linked with a restriction end digested with restriction enzymes, such as HinPI, MaeII, MspI and TthHB8I.

Separately, a 5 μM aqueous solution of the oligonucleotide shown by SEQ ID NO: 60 was prepared and used as the primer for the cassette.

(3) Synthesis of Petunia Petal cDNA

Four plants of the delphinidin-type and two plants of the cyanidin-type were selected from the backcrossed population produced in Example 2, and cDNAs were synthesized using mRNAs extracted from the petals of each plant according to the methods described in Example 1 (2) and (3). Similarly, cDNAs were synthesized from petals of Falcon Blue, Falcon Red, Falcon Salmon, and Purple Joy.

(4) TthHB8I Digestion of cDNA and Linkage to Cassette

An aliquot of 0.1 μg of each of the ten types of cDNAs obtained in (3) above was dissolved in 50 μl of H buffer, and one unit of the restriction enzyme TthHB8I (Takara Shuzo Co., Ltd.) was added. The reaction was carried out at 65° C. for one hour. Then, the reaction mixture was mixed with 5 μl of phenol/chloroform (1:1) mixture, followed by addition of 150 μl of ethanol. The resulting mixture was allowed to stand at −80° C. for 10 minutes, and centrifuged at 10,000×g for 10 minutes. The obtained precipitate was washed with 200 μl of 70% ethanol, and dried under vacuum. The obtained DNA was dissolved in 9 μl of TE buffer.

After adding 1 μl of the cassette to each DNA solution, ligation reaction was carried out at 16° C. for 30 minutes using the DNA Ligation Kit (Takara Shuzo Co., Ltd.) according to the instructions provided by the manufacturer. The volume of the reaction mixture was 60 μl.

(5) PCR Between K Primers and the Primer for Cassette

By the use of each of the above reaction mixtures as a template, the sequence to a near restriction site can be amplified by PCR between a K primer (01 to 15) and the primer for the cassette.

An aliquot of 1 μl of each of the above-mentioned reaction mixtures, which was used as a template, was added to 1 μl of a K primer and 1 μl of the primer for the cassette, and mixed with 25 μl of PCR buffer. The mixture was transferred into a 0.5-ml microcentrifugation tube, 0.5 unit of Taq DNA polymerase (Perkin-Elmer Cetus) was added thereto, and 10 μl of mineral oil was layered over the mixture. The reaction was carried out using the DNA Thermal Cycler (Perkin-Elmer Cetus) for 40 cycles with the cycle profile consisting of 30 seconds at 93° C. and 1 minute at 55° C. According to the methods described in the book by Maniatis et al., the PCR products were subjected to 10% polyacrylamide gel electrophoresis, and DNA bands were stained with ethidium bromide and examined under UV light.

As a result, in the SSP-PCR using K14 primer, a DNA band of about 85 bp was obtained when one of the six types of cDNAs obtained from Falcon Blue, Purple Joy, and four delphinidin-type backcrossed plants was used as the template. On the other hand, the band was not detected when one of the four types of cDNAs obtained from Falcon Red, Falcon Salmon, and two cyanidin-type backcrossed plants was used as the template. That is, it was demonstrated that the presence/absence of the SSP-PCR products of about 85 bp was genetically linked to the presence/absence of said enzyme activity. When the other primers were used, no such product was detected. As the K14 primer was designed based on the core sequence shown by SEQ ID NO: 43, it was suggested that the sequence shown by SEQ ID NO: 43 was a part of the DNA sequence encoding the polypeptide which had said enzyme activity.

(6) Synthesis of J14 Primer

On the basis of the core sequence of cytochrome P450 shown by SEQ ID NO: 43, according to which K14 primer was synthesized, a primer shown by SEQ ID NO: 62 was chemically synthesized using the DNA Synthesizer Cyclone Plus (Milligen/Biosearch). The primer was named J14 primer, and used in a 5 μM aqueous solution.

(7) HinPI Digestion of cDNA and Linkage to Cassette

An aliquot of 0.1 μg of each of the ten types of cDNAs obtained in (3) above was dissolved in 50 μl of M buffer [10 mM Tris hydrochloride buffer (pH 7.5), 10 mM magnesium chloride, 1 mM dithiothreitol, 50 mM sodium chloride], and one unit of the restriction enzyme HinPI (New England Biolabs) was added. The reaction was carried out at 37° C. for one hour. Then, the reaction mixture was mixed with 5 μl of phenol/chloroform (1:1) mixture, followed by addition of 150 μl of ethanol. The resulting mixture was allowed to stand at −80° C. for 10 minutes, and centrifuged at 10,000×g for 10 minutes. The obtained precipitate was washed with 200 μl of 70% ethanol, and dried under vacuum. The obtained DNA was dissolved in 9 μl of TE buffer. After adding 1 μl of the cassette to each DNA solution, ligation reaction was carried out at 16° C. for 30 minutes using the DNA Ligation Kit (Takara Shuzo Co., Ltd.) according to the instructions provided by the manufacturer. The volume of the reaction mixture was 60 μl.

(8) PCR Between J14 Primer and the Primer for Cassette

An aliquot of 1 μl of each of the above-mentioned reaction mixtures, which was used as a template, was added to 1 μl of J14 primer and 1 μl of the primer for the cassette, and mixed with 25 μl of PCR buffer. The mixture was transferred into a 0.5-ml microcentrifugation tube, 0.5 unit of Taq DNA polymerase (Perkin-Elmer Cetus) was added thereto, and 10 μl of mineral oil was layered over the mixture. The reaction was carried out using the DNA Thermal Cycler (Perkin-Elmer Cetus) for 40 cycles with the cycle profile consisting of 30 seconds at 93° C. and 1 minute at 55° C. According to the methods described in the book by Maniatis et al., the PCR products were subjected to 10% polyacrylamide gel electrophoresis, and DNA bands were stained with ethidium bromide and examined under UV light.

As a result, in the SSP-PCR using J14 primer, a DNA band of about 280 bp was obtained when one of the six types of cDNAs obtained from Falcon Blue, Purple Joy, and four delphinidin-type backcrossed plants was used as the template. On the other hand, the band was not detected when one of the four types of cDNAs obtained from Falcon Red, Falcon Salmon, and two cyanidin-type backcrossed plants was used as the template. That is, it was demonstrated that the presence/absence of the SSP-PCR products of about 280 bp was genetically linked to the presence/absence of said enzyme activity. It was strongly suggested that the core sequence shown by SEQ ID NO: 43 was a part of the DNA sequence encoding the polypeptide which had said enzyme activity.

EXAMPLE 4

Construction and Sequencing of Plasmid pEAK14

A library is constructed by incorporating petunia petal cDNAs into an appropriate vector. The library is searched using the SSP-PCR product of about 280 bp obtained in Example 3 as a probe, and the sequence of a clone which hybridizes with the probe is determined.

(1) Construction of Petunia Petal cDNA Library

One microgram of cDNA prepared from the petals of petunia (Falcon Blue) in Example 1 (3) was cloned using the cDNA Cloning System λgt10·RPN1257 (Amersham Co., Ltd.) according to the instructions provided by the manufacturer. The final product was subjected to the packaging reaction using the λDNA in vitro packaging kit Giga Pack Gold (Stratagene Co., Ltd.) according to the instructions provided by the manufacturer. Cells of E. coli NM 514 (Amersham Co., Ltd.) were infected with the appropriately diluted packaging products according to the instructions provided by the manufacturer, and spread on LB agar medium [1% Bacto Tryptone (Difco Laboratories), 0.5% Bacto Yeast Extract (Difco Laboratories), 1% sodium chloride, 1.5% Bacto Agar (Difco Laboratories)] in plastic plates of 15 cm in diameter (Iwaki Glass Co., Ltd.) to obtain about 10,000 plaques per plate. A total of five plates were prepared.

(2) Radiolabeling of DNA Probe

A portion containing the PCR product of about 280 bp obtained in Example 3 was cut out from the polyacrylamide gel, and the PCR product was extracted and purified according to the method described in the book by Maniatis et al. Approximately 50 ng of the purified DNA was labeled with [α-$^{32}$P]dCTP (Amersham Co., Ltd.) using the Multiprime™ DNA Labeling System (Amersham Co., Ltd.) according to the instructions provided by the manufacturer.

(3) Screening by Plaque Hybridization

The plaques on the five plates obtained in Example 4 (1) were transferred onto nylon filters (MSI Co., Ltd.), alkali-denatured, and fixed by heating at 90° C. for 3 hours, according to the methods described in the book by Maniatis et al. The labeled DNA probe prepared in Example 4 (2) was added to the filters and hybridization was carried out according to the method described in the book by Maniatis et al. At the final step, the filters were washed with 0.1×SSC (15 mM sodium chloride, 1.5 mM sodium citrate, pH 7.0) at 60° C., and were analyzed by autoradiography to search for positive clones. As a result, 11 positive clones were obtained. One of the clones was selected, and according to the methods described in the book by Maniatis et al., phages were multiplied and DNA was extracted from them.

(4) Subcloning into Plasmid Vectors

About 5 μg of the above-mentioned phage DNA was dissolved in 20 μl of H buffer, and 10 units of the restriction enzyme BamHI (Takara Shuzo Co., Ltd.) was added. The reaction was carried out at 30° C. for 2 hours. After separation of the reaction products by electrophoresis through a 0.8% GTG agarose gel (Takara Shuzo Co., Ltd.), a portion containing the inserted DNA fragment of about 1.9 kb was cut out. The DNA fragment was extracted and purified using the SUPREC™-01 (Takara Shuzo Co., Ltd.) according to the instructions provided by the manufacturer.

The obtained DNA fragment was dissolved in 10 μl of TE buffer and 0.2 μg of pUC18 BamHI BAP (Pharmacia Co., Ltd.) was added. Ligation reaction was carried out at 16° C. for 30 minutes using the DNA Ligation Kit (Takara Shuzo Co., Ltd.) according to the instructions provided by the manufacturer. The volume of the reaction mixture was 60 μl. Highly competent cells of E. coli JM109 (Toyobo Co., Ltd.) were transformed with 2 μl of the reaction mixture according to the instructions provided by the manufacturer. The cells were cultured at 37° C. for 20 hours on X-gal ampicillin LB agar medium according to the method described in the book by Maniatis et al. One of the formed white colonies was isolated and cultured, and plasmid DNA was extracted from the culture and purified. The obtained plasmid was named pEAK14.

(5) Determination of DNA Sequence

The nucleotide sequence of about 1.9 kb which was contained in the plasmid pEAK14 and derived from petunia cDNA was determined by the Model 373A DNA Sequencing System (ABI Co., Ltd.) using the Deletion Kit for Kilosequence (Takara Shuzo Co., Ltd.) and the Taq Dideoxy™ Terminator Cycle Sequencing Kit (ABI Co., Ltd.) according to the instructions provided by the manufacturers. The sequence was analyzed using a sequence analysis software, DNASIS™ (Hitachi Software Engineering Co., Ltd.).

As a result, the DNA sequence of 1824 bp shown by SEQ ID NO: 1 was obtained. This sequence contained an open reading frame starting at the 116th nucleotide and ending at the 1633rd nucleotide, and coding for a polypeptide consisting of 506 amino acid residues. The amino acid sequence of the polypeptide showed approximately 33% homology to that of cytochrome P450 of avocado which had been reported (Proc. Natl. Acad. Sci. USA, vol.87, p.3904–3908, 1990).

This open reading frame was named AK14 sequence.

EXAMPLE 5

Introduction of the AK14 Sequence into Plant Expression Vectors (1) Deletion of ATG Sequence in 5' Non-coding Region An aliquot of 2 μg of the plasmid pEAK14 obtained in Example 4 (4) was dissolved in 20 μl of H buffer, and 10 units of the restriction enzyme BamHI (Takara Shuzo Co., Ltd.) was added. The reaction was carried out at 30° C. for 2 hours. The reaction products were separated by electrophoresis through a 0.8% GTG agarose gel (Takara Shuzo Co., Ltd.), and a portion containing the inserted DNA fragment of about 1.9 kb was cut out. Then, the DNA fragment was extracted and purified using the SUPREC™-01 (Takara Shuzo Co., Ltd.) according to the instructions provided by the manufacturer.

The obtained DNA fragment was dissolved in 50 μl of BAL31 buffer [20 mM Tris hydrochloride buffer (pH 8.0), 600 mM sodium chloride, 12 mM calcium chloride, 12 mM magnesium chloride, 1 mM EDTA], and one unit of BAL31 nuclease S (Takara Shuzo Co., Ltd.) was added. The reaction was carried out at 30° C. for one minute, followed by addition of 5 μl of phenol:chloroform (1:1) mixture to terminate the reaction. After addition of 150 μl of ethanol, the reaction mixture was allowed to stand at −80° C. for 10 minutes, and then centrifuged at 10,000×g for 10 minutes. The obtained precipitate was washed with 200 μl of 70% ethanol, and dried under vacuum. The obtained DNA was dissolved in 50 μl of the Klenow buffer [50 mM Tris hydrochloride buffer (pH 7.5), 10 mM magnesium chloride, 1 mM dithiothreitol, 100 μM dATP, 100 μM dCTP, 100 μM dGTP, 100 μM dTTP], and one unit of Klenow fragment (Takara Shuzo Co., Ltd.) was added. The reaction was carried out at 30° C. for 30 minutes. After addition of 150 μl of ethanol, the reaction mixture was allowed to stand at −80° C. for 10 minutes, and then centrifuged at 10,000×g for 10 minutes. The obtained precipitate was washed with 200 μl of 70% ethanol, and dried under vacuum. The obtained DNA was dissolved in 10 μl of TE buffer.

(2) Subcloning into Plasmid Vectors

An aliquot of 1 μg of pUC19 (Pharmacia Co., Ltd.) was dissolved in 50 μl of Sma buffer [10 mM Tris hydrochloride buffer (pH 7.5), 10 mM magnesium chloride, 1 mM dithiothreitol, 20 mM potassium chloride], and 10 units of the restriction enzyme SmaI (Takara Shuzo Co., Ltd.) was added. The reaction was carried out at 30° C. for 2 hours. After addition of 150 μl of ethanol, the reaction mixture was allowed to stand at −80° C. for 10 minutes, and then centrifuged at 10,000×g for 10 minutes. The obtained precipitate was washed with 200 μl of 70% ethanol, and dried under vacuum. The obtained DNA was dissolved in 50 μl of CIP buffer [50 mM Tris hydrochloride buffer (pH 9.0), 1 mM magnesium chloride, 0.1 mM zinc chloride, 1 mM spermidine], and 0.1 unit of calf intestine alkaline phosphatase (Boehringer Mannheim GmbH) was added. The reaction was carried out at 37° C. for 30 minutes, and then at 56° C. for 30 minutes, followed by addition of 5 μl of phenol:chloroform (1:1) mixture to terminate the reaction. After addition of 150 μl of ethanol, the reaction mixture was allowed to stand at −80° C. for 10 minutes, and then centrifuged at 10,000×g for 10 minutes. The obtained precipitate was washed with 200 μl of 70% ethanol, and dried under vacuum. The obtained DNA was dissolved in 10 μl of TE buffer [10 mM Tris hydrochloride buffer (pH 7.5), 1 mM EDTA] to obtain a vector DNA solution.

An aliquot of 1 μl of the above-mentioned vector DNA solution and 2 μl of the DNA solution obtained in Example 5 (1) were mixed and subjected to ligation at 16° C. for 30 minutes using the DNA Ligation Kit (Takara Shuzo Co., Ltd.) according to the instructions provided by the manufacturer. The volume of the reaction mixture was 18 μl. Highly competent cells of E. coli JM109 (Toyobo Co., Ltd.) were transformed with 2 μl of the reaction mixture according to the instructions provided by the manufacturer. The cells were cultured at 37° C. for 20 hours on X-gal ampicillin LB agar medium according to the method described in the book by Maniatis et al. One of the formed white colonies was isolated and cultured, and plasmid DNA was extracted from the culture and purified. The obtained plasmid was named pEAK14S.

The nucleotide sequence of the region bound to the SmaI site derived from pUC19 vector in pEAK14S was analyzed. As a result, it was shown that the sequence of pEAK14S lacked the 1st to the 91st nucleotides of the sequence shown by SEQ ID NO: 1. It was also revealed that the direction of the insertion was such that the BamHI site of pUC19 vector was linked to the amino terminus of the AK14 sequence.

(3) Subcloning into a Plant Expression Vector, pBI121

An aliquot of 1 μg of pEAK14S was dissolved in 50 μl of M buffer, and 10 units of the restriction enzyme SacI (Takara Shuzo Co., Ltd.) and 10 units of the restriction enzyme XbaI (Takara Shuzo Co., Ltd.) were added. The reaction was carried out at 37° C. for 2 hours. The reaction products were separated by electrophoresis through a 0.8% GTG agarose gel (Takara Shuzo Co., Ltd.), and a portion containing the inserted DNA fragment of about 1.9 kb was cut out. Then, the DNA fragment was extracted and purified using the SUPREC™-01 (Takara Shuzo Co., Ltd.) according to the instructions provided by the manufacturer. The obtained DNA fragment was dissolved in 10 μl of TE buffer.

Similarly, an aliquot of 1 μg of a plant expression vector, pBI121 (GUS Gene Fusion System: Clonetech Co., Ltd.) was dissolved in 50 μl of M buffer, and 10 units of the restriction enzyme SacI (Takara Shuzo Co., Ltd.) and 10 units of the restriction enzyme XbaI (Takara Shuzo Co., Ltd.) were added. The reaction was carried out at 37° C. for 2 hours. The reaction products were separated by electrophoresis through a 0.8% GTG agarose gel (Takara Shuzo Co., Ltd.), and a portion containing the vector DNA fragment of about 11 kb was cut out. Then, the vector DNA fragment was extracted and purified using the SUPREC™-01 (Takara Shuzo Co., Ltd.) according to the instructions provided by the manufacturer. The obtained vector DNA fragment was dissolved in 10 μl of TE buffer.

An aliquot of 1 μl of the above-mentioned TE buffer containing the AK14 DNA fragment of about 1.9 kb and 1 μl of the above-mentioned TE buffer containing the vector DNA fragment of about 11 kb were mixed, and subjected to ligation at 16° C. for 30 minutes using the DNA Ligation Kit (Takara Shuzo Co., Ltd.) according to the instructions provided by the manufacturer. The volume of the reaction mixture was 12 μl. Highly competent cells of E. coli JM109 (Toyobo Co., Ltd.) were transformed with 2 μl of the reaction mixture according to the instructions provided by the manufacturer. The cells were cultured at 37° C. for 20 hours on kanamycin LB agar medium [1% Bacto Tryptone (Difco Laboratories), 0.5% Bacto Yeast Extract (Difco Laboratories), 1% sodium chloride, 50 μg/ml kanamycin, 1.5% Bacto Agar (Difco Laboratories)] according to the method described in the book by Maniatis et al. One of the formed colonies was isolated and cultured, and plasmid DNA was extracted from the culture and purified. The obtained plasmid was named pBAK14.

(4) Introduction of pBAK14 into *Agrobacterium tumefaciens* LBA4404

The plasmid pBAK14 was introduced into *Agrobacterium tumefaciens* LBA4404 by triparental mating using the GUS Gene Fusion System (Clonetech Co., Ltd.) according to the instructions provided by the manufacturer. *E. coli* JM109 strain which carries pBAK14 and *E. coli* HB101 strain which carries pRK2013 (Clonetech Co., Ltd.) were cultured, respectively, in 1 ml of kanamycin LB liquid medium [1% Bacto Tryptone (Difco Laboratories), 0.5% Bacto Yeast Extract (Difco Laboratories), 1% sodium chloride, 50 µg/ml kanamycin] with shaking at 37° C. for 12 hours. Separately, *Agrobacterium tumefaciens* LBA4404 which carries pAL4404 (Clonetech Co., Ltd.) was cultured in 1 ml of streptomycin LB liquid medium [1% Bacto Tryptone (Difco Laboratories), 0.5% Bacto Yeast Extract (Difco Laboratories), 1% sodium chloride, 300 µg/ml streptomycin] with shaking at 28° C. for 36 hours. Three types of cultured cells were individually collected by centrifugation at 5,000×g for 10 minutes, washed with 1 ml of water, and suspended in small amount of water. The suspensions were mixed together, and the whole of the combined suspension was spread on LB agar medium and incubated at 28° C. for 20 hours. The obtained cells were applied on LB agar medium containing 50 µg/ml kanamycin and 300 µg/ml streptomycin, and incubated at 28° C. over 2 nights. One of the formed colonies was isolated to obtain *Agrobacterium tumefaciens* LBA4404 carrying both pBAK14 and pAL4404.

EXAMPLE 6

Introduction of the AK14 Sequence into Tobacco and its Expression (1) Introduction into Tobacco Using a Microorganism of the Genus Agrobacterium

*Agrobacterium tumefaciens* LBA 4404 strain carrying pBAK14 and pAL4404 which was obtained in Example 5 was cultured in 10 ml of LB liquid medium [1% Bacto Tryptone (Difco Laboratories), 0.5% Bacto Yeast Extract (Difco Laboratories), 1% sodium chloride] containing 50 µg/ml kanamycin and 300 µg/ml streptomycin, with shaking at 28° C. for 40 hours. The cultured cells were collected by centrifugation at 5,000×g for 10 minutes, washed with 10 ml of water, and then suspended in an equal amount of water.

Leaves of tobacco (*Nicotiana tabacum* cv. petit Havana SR-1) aseptically subcultured at 25° C. were cut into one centimeter squares, soaked in the above-mentioned cell suspension, and wiped with sterilized filter paper. The leaves were placed on MS medium containing 1 µg/ml 6-benzyladenine, 0.3 µg/ml 1-naphthaleneacetic acid, 3% sucrose, and 0.2% Gelrite (Physiol. Plant., vol.15, p.473–497, 1962) (hereinafter referred to as the solid PD4 medium) with the abaxial side up, and cultured at 25° C. for 2 days under continuous light illumination at 2,500 lux. Then, the leaves were transplanted to the solid PD4 medium containing 500 µg/ml Claforan (for injection, Hoechst Japan Co., Ltd.) and 200 µg/ml kanamycin for culturing, and transplanted to the same medium every 2 weeks afterward. About one month after the start of culturing, adventitious buds were induced. The buds were cut off and subcultured on MS medium containing 500 µg/ml Claforan and 50 µg/ml kanamycin to induce rooting. Plants which took roots were transferred into pots, after checked for their aseptic condition, and cultivated at 25° C. in an artificial weather system. Transgenic plants were thus obtained.

(2) Detection of Enzyme Activity in Leaves of Tobacco which had been Transformed (hereinafter referred to as the transgenic tobacco)

Microsome fraction was prepared from 20 g of the transgenic tobacco leaves obtained as above according to the method described in Example 2 (3), and flavonoid-3',5'-hydroxylase activity in the fraction was determined. As a control, microsome fraction prepared from non-transgenic tobacco leaves was used. As a result, said enzyme activity, which catalyzes the conversion of dihydroquercetin to dihydromyricetin, was detected only in the microsome fraction of the transgenic tobacco.

(3) Change in Pigments in Petals of the Transgenic Tobacco

Anthocyanidins were prepared from petals of the transgenic and non-transgenic tobacco plants, respectively, according to the method described in Example 2 (1), and analyzed. As a result, only cyanidin was detected in the non-transgenic tobacco, whereas cyanidin and delphinidin were detected in almost the same amounts in the transgenic tobacco.

The flower colors were compared with The Japan Color Standard For Horticultural Plants (Japan Color Research Institute). The color of flowers of the transgenic tobacco corresponded to Color No. 8904 or 8905, and that of the non-transgenic tobacco corresponded to Color No. 9503 or 9504. That is, flowers of the transgenic tobacco showed more bluish color.

EXAMPLE 7

Introduction of the AK14 Sequence into a Petunia Cultivar with Pink Flowers and its Expression (1) Introduction into Petunia Using a Microorganism of the Genus Agrobacterium Kanamycin-resistant transgenic plants were obtained by infecting leaves of aseptically subcultured petunia (*Petunia hybrida* cv. Falcon Pinkvein: Sakata Seed Corporation) with *Agrobacterium tumefaciens* LBA4404 strain which carries pBAK14 and pAL4404 according to a method similar to that used in Example 6.

(2) Change in Pigments in Petals of the Transgenic Petunia

Anthocyanidins were prepared from petals of the above-mentioned transgenic petunia according to the method described in Example 2 (1), and compared with those prepared from the control, non-transgenic petunia (Falcon Pinkvein). As a result, little malvidin or delphinidin was detected in the non-transgenic petunia. On the other hand, the transgenic petunia had both of them as major components. The major component in the control plants was peonidin.

The flower colors at the center area of petals were compared with The Japan Color Standard For Horticultural Plants (Japan Color Research Institute). The color of flowers of the transgenic petunia corresponded to Color No. 9206 or 9207, and that of the non-transgenic petunia (Falcon Pinkvein) corresponded to Color No. 9204 or 9205. That is, flowers of the transgenic petunia showed more bluish color.

Example 8

Introduction of the AK14 Sequence into Rose and its Expression (1) Introduction into Rose Using a Microorganism of the Genus Agrobacterium Leaves of aseptically subcultured rose (*Rosa hybrida* cv. deep red) were infected with *Agrobacterium tumefaciens* LBA4404 strain carrying pBAK14 and pAL4404 according to a method similar to that used in Example 6 (1). The leaves were placed on MS medium containing 0.01 µg/ml 6-benzyladenine, 10 µg/ml 2,4-dichlorophenoxyacetic acid, 3% sucrose, and 0.2% Gelrite (hereinafter referred to as the solid BE medium), and cultured at 25° C. for 2 days under continuous light illumination at 2,500 lux. Then, the leaves were transplanted to the solid BE medium containing 500 µg/ml Claforan, and after 7 days, transplanted to the solid BE medium containing 500 µg/ml Claforan and 200 µg/ml kanamycin. Thereafter, the leaves were transplanted to the same medium every 2 weeks. After about 2 months, approximately 20 g of kanamycin-resistant callus was obtained.

(2) Expression of Enzyme Activity in the Rose Callus

Microsome fraction was prepared from the callus obtained in Example 8 (1) according to the method described in Example 2 (3), and flavonoid-3',5'-hydroxylase activity in the fraction was determined. As a control, microsome fraction prepared from untransformed callus of rose was used. As a result, said enzyme activity, which catalyzes the conversion of dihydroquercetin to dihydromyricetin, was detected only in the microsome fraction of the transformed callus.

EXAMPLE 9

Introduction of the AK14 Sequence into Carnation and its Expression (1) Introduction of pBAK14 into *Agrobacterium rhizogenes* NIAES1724 Strain According to a method similar to that described in Example 5 (4), pBAK14 was introduced into *Agrobacterium rhizogenes* NIAES1724 strain (obtained from National Institute of Agrobiological Resources, the Japanese Ministry of Agriculture, Forestry and Fisheries). In this example, JM103 was used as the *E. coli* strain, and 25 µg/ml nalidixic acid (Sigma Co., Ltd.) was used instead of streptomycin.

(2) Introduction of the AK14 Sequence into Carnation Using a Microorganism of the Genus Agrobacterium Petals cut off from buds of carnation (*Dianthus caryophillus* cv. Nora) were infected with *Agrobacterium rhizogenes* NIAES1724 carrying pBAK14 according to a method similar to that described in Example 6 (1). The infected petals were placed on solid MS medium containing 0.3 µg/ml 6-benzyladenine, 0.3 µg/ml naphthaleneacetic acid, 3% sucrose, and 0.2% Gelrite, and cultured at 25° C. for 3 days under continuous light illumination at 2,500 lux. Then, the petals were transplanted to the same medium containing 250 µg/ml Claforan, and after 7 days, transplanted to the same medium containing 250 µg/ml Claforan and 300 µg/ml kanamycin. Thereafter, the petals were transplanted to the same medium every 2 weeks. After about 4 months, approximately 10 g of kanamycin-resistant hairy roots were obtained.

(3) Expression of Enzyme Activity in Hairy Roots of Carnation

Microsome fraction was prepared from the hairy roots obtained in Example 9 (2) according to the method described in Example 2 (3), and flavonoid-3',5'-hydroxylase activity in the fraction was determined. As a control, microsome fraction prepared from hairy roots infected with *Agrobacterium rhizogenes* NIAES1724 strain which did not carry pBAK14 was used. As a result, said enzyme activity, which catalyzes the conversion of dihydroquercetin to dihydromyricetin, was detected only in the microsome fraction of the transformed hairy roots.

EXAMPLE 10

Detection of AK14 Homologous Sequences in Genomic DNAs of Heterogeneous Plants (1) Preparation of Plant Genomic DNA Ten to twenty grams of green leaves of each of the following plants was freeze-dried, and their genomic DNAs were extracted according to the method described in DNA Cloning A Practical Approach, vol.2, p.103, 1985, IRL Press: petunia (*Petunia hybrida* cv. Purple Joy: NPI Seeds), nicotiana (*Nicotiana affinis* cv. F1 Domino: Daiichi Seed Co., Ltd.), Japanese gentian (*Gentiana triflora* cv. Japonica), sweet pea (*Lathyrus odoratus* cv. Royal Deep Blue: Daiichi Seed Co., Ltd.), pansy (*Viola tricolor*, blue cultivar), primrose (*Primula polyantha*, purple cultivar), Russell prairie gentian (*Eustoma russellianum* cv. Royal Light Purple: Takii Seed Co., Ltd.), campanula (*Campanula medium*, light purple cultivar), delphinium (*Delphinium hybridum*, pale blue cultivar), and hyacinth (*Hyacinthus orientalis*, purple cultivar).

(2) Preparation of Genomic DNA Blots

An aliquot of 5 µg of each of the genomic DNAs obtained in Example 10 (1) was dissolved in 20 µl of H buffer, and 10 units of the restriction enzyme EcoRV (Takara Shuzo Co., Ltd.) was added. The reaction was carried out at 37° C. for 2 hours. According to the method described in the book by Maniatis et al, the digested DNA was subjected to 0.8% agarose gel electrophoresis, alkali-denatured, and neutralized. Then, the DNA was transferred onto nylon filters (MSI Co., Ltd.), and fixed by heating at 90° C. for 3 hours for fixation to prepare genomic DNA blots.

(3) Radiolabeling of AK14 Sequence Probe

An aliquot of 1 µg of pEAK14 obtained in Example 4 was dissolved in 20 µl of H buffer, and 10 units of the restriction enzyme BamHI (Takara Shuzo Co., Ltd.) was added. The reaction was carried out at 37° C. for 2 hours. The reaction products were separated by electrophoresis through a 0.8% GTG agarose gel (Takara Shuzo Co., Ltd.), and a portion containing the inserted DNA fragment of about 1.9 kb was cut out. The inserted DNA fragment was extracted and purified using the SUPREC™-01 (Takara Shuzo Co., Ltd.) according to the instructions provided by the manufacturer. An aliquot of 50 ng of the DNA fragment containing the AK14 sequence was labeled with [α-$^{32}$P]dCTP (Amersham Co., Ltd.) using the Multiprime™ DNA Labeling System (Amersham Co., Ltd.) according to the instructions provided by the manufacturer.

(4) Hybridization

The genomic DNA blots obtained in Example 10 (2) were hybridized with the labeled probe of (3) according to the method described in the book by Maniatis et al. At the final step, the filters were washed twice with 2×SSC (0.3 M sodium chloride, 0.03 M sodium citrate, pH 7.0) at 50° C. for 30 minutes. The obtained filters were examined by autoradiography using X-ray films (New RX: Fuji Photo Film Co., Ltd.). As a result, the DNAs prepared from petunia (Purple Joy), nicotiana, Japanese gentian, Russell prairie gentian, and campanula showed a clear band. The DNAs prepared from sweet pea and primrose showed a band hybridized with the probe though unclear. That is, the result showed that homologous sequences which hybridize with the AK14 sequence existed in the genomic DNAs of these plants.

EXAMPLE 11

Detection of AK14 Homologous Sequences in Petal cDNAs of Heterogeneous Plants (1) Preparation of Petal cDNA About 10 g of petals was collected from buds of each of the following plants; petunia (*Petunia hybrida* cv. Purple Joy: NPI Seeds Co., Ltd.), nicotiana (*Nicotiana affinis* cv. F1 Domino: Daiichi Seed Co., Ltd.), Japanese gentian (*Gentiana triflora* cv. Japonica), Russell prairie gentian (*Eustoma russellianum* cv. Royal Light Purple: Takii Seed Co., Ltd.), and campanula (*Campanula medium*, light purple cultivar). mRNAs were extracted from the petals according to the method described in Example 1 (2). By using the obtained mRNAs as templates, double strand cDNAs were synthesized using the cDNA Synthesis System Plus RPN1256 (Amersham Co., Ltd.) according to the instructions provided by the manufacturer.

(2) Preparation of cDNA Blots

According to the method described in the book by Maniatis et al, about 0.1 μg of each of the above-mentioned cDNAs was subjected to 0.8% agarose gel electrophoresis, alkali-denatured, and neutralized. Then, the cDNA was transferred onto nylon filters (MSI Co., Ltd.), and fixed by heating at 90° C. for 3 hours to prepare cDNA blots.

(3) Hybridization

A radiolabeled AK14 sequence probe was prepared according to a method similar to that used in Example 10 (3), and hybridized with each of the above-mentioned cDNA blots according to a method similar to that used in Example 10 (4). At the final step, the filters were washed twice with 2×SSC at 50° C. for 30 minutes, and then examined by autoradiography. As a result, each plant showed a clear band at the location corresponding to about 2 kb. That is, it was demonstrated that analogous sequences which hybridize with the AK14 sequence existed in the petal cDNAs of these plants.

EXAMPLE 12

Cloning of the AK14 Homologous Sequence from Russell Prairie Gentian and Campanula (1) Construction of Petal cDNA Library About 20 g of petals was collected from buds of Russell prairie gentian (*Eustoma russellianum* cv. Royal Light Purple: Takii Seed Co., Ltd.) and campanula (*Campanula medium*, light purple cultivar), and mRNAs were extracted from them, respectively, according to the method described in Example 1 (2). By using the obtained mRNAs as templates, double strand cDNAs were synthesized and cloned into λgt22 vectors using the Superscript™ Lambda System (BRL Life Technologies Co., Ltd.) according to the instructions provided by the manufacturer.

Each final product was subjected to the packaging reaction using the λDNA in vitro packaging kit Giga Pack Gold (Stratagene Co., Ltd.) according to the instructions provided by the manufacturer. Cells of *E. coli* Y1090 (r⁻) (BRL Life Technologies Co., Ltd.) were infected with the appropriately diluted packaging products according to the instructions provided by the manufacturer, and spread on LB agar medium [1% Bacto Tryptone (Difco Laboratories), 0.5% Bacto Yeast Extract (Difco Laboratories), 1% sodium chloride, 1.5% Bacto Agar (Difco Laboratories)] in plastic plates of 15 cm in diameter (Iwaki Glass Co., Ltd.) to obtain about 10,000 plaques per plate. Five plates were prepared for Russell prairie gentian and campanula, respectively, to obtain cDNA libraries.

(2) Screening by Plaque Hybridization

The plaques on the five plates obtained in Example 12 (1) were transferred onto nylon filters (MSI Co., Ltd.), alkali-denatured, and fixed by heating at 90° C. for 3 hours according to the methods described in the book by Maniatis et al. The radiolabeled probe DNA prepared by a method similar to that used in Example 11 (3) was added to the filters and hybridization was carried out according to the method described in the book by Maniatis et al. At the final step, the filters were washed with 2×SSC (0.3 M sodium chloride, 0.03 M sodium citrate, pH 7.0) at 50° C., and were examined by autoradiography to search for positive clones. As a result, 12 and 7 positive clones were obtained from the library of Russell prairie gentian and that of campanula, respectively. One clone was selected from each library, and according to the method described in the book by Maniatis et al, phages were multiplied and DNAs were extracted from them.

About 5 μg of each phage DNA was dissolved in 20 μl of H buffer, and 10 units of the restriction enzyme NotI (Takara Shuzo Co., Ltd.) and 10 units of the restriction enzyme SalI (Takara Shuzo Co., Ltd.) were added. The reaction was carried out at 37° C. for 2 hours. The reaction products were separated by electrophoresis through a 0.8% GTG agarose gel (Takara Shuzo Co., Ltd.), and a portion containing the inserted DNA fragment of about 2 kb was cut out from each gel. The DNA fragments were extracted and purified using the SUPREC™-01 (Takara Shuzo Co., Ltd.) according to the instructions provided by the manufacturer, and dissolved in 10 μl of TE buffer, respectively.

(3) Subcloning into Plasmid Vectors

About 1 μg of DNA of a plasmid vector, pBluescriptIIKS+ (Stratagene Co., Ltd.) was dissolved in 20 μl of H buffer, and 10 units of the restriction enzyme NotI (Takara Shuzo Co., Ltd.) and 10 units of the restriction enzyme SalI (Takara Shuzo Co., Ltd.) were added. The reaction was carried out at 37° C. for 2 hours. The reaction products were separated by electrophoresis through a 0.8% GTG agarose gel (Takara Shuzo Co., Ltd.), and a portion containing the vector DNA fragment of about 3 kb was cut out. The DNA fragment was extracted and purified using the SUPREC™-01 (Takara Shuzo Co., Ltd.) according to the instructions provided by the manufacturer, and dissolved in 10 μl of TE buffer.

To 4 μl each of the two types of inserted DNA fragments obtained in Example 12 (2) was added 1 μl of the above-mentioned vector DNA fragment, respectively, and ligation was carried out at 16° C. for 30 minutes using the DNA Ligation Kit (Takara Shuzo Co., Ltd.) according to the instructions provided by the manufacturer. The volume of each reaction mixture was 30 μl. Highly competent cells of *E. coli* JM109 (Toyobo Co., Ltd.) were transformed with 2 μl each of the reaction mixtures, respectively, according to the instructions provided by the manufacturer. The transformed cells were cultured at 37° C. for 20 hours on X-gal ampicillin LB agar medium according to the method described in the book by Maniatis et al. From each culture, one of the white colonies formed was isolated and cultured, and plasmid DNA was extracted from the culture and purified. The plasmid derived from the library of Russell prairie gentian was named pETg1, and that from the library of campanula was named pEKa1.

(4) Determination of DNA Sequence

The nucleotide sequences of the DNA fragments which were derived from the petal cDNAs and contained in the plasmids pETg1 and pEKa1 were determined by the Model 373A DNA Sequencing System (ABI Co., Ltd.) using the Deletion Kit for Kilosequence (Takara Shuzo Co., Ltd.) and the Taq Dideoxy™ Terminator Cycle Sequencing Kit (ABI Co., Ltd.) according to the instructions provided by manufacturers. The sequences were analyzed using a sequence analysis software, DNASIS™ (Hitachi Software Engineering Co., Ltd.).

As a result, the DNA sequence of 2174 bp shown by SEQ ID NO: 63 was obtained from Russell prairie gentian. This sequence contained an open reading frame starting at the 92nd nucleotide and ending at the 1621st nucleotide, and coding for a polypeptide consisting of 510 amino acid residues. The amino acid sequence of the polypeptide showed 74% homology to that of AK14. This open reading frame was named Tg1 sequence.

The DNA sequence of 1927 bp shown by SEQ ID NO: 64 was obtained from campanula. This sequence contained an open reading frame starting at the 180th nucleotide and ending at the 1748th nucleotide, and coding for a polypeptide consisting of 523 amino acid residues. The amino acid sequence of the polypeptide showed 66% homology to that of AK14. This open reading frame was named Ka1 sequence.

EXAMPLE 13

Introduction of Tg1 and Ka1 into Plant Expression Vectors (1) Subcloning into Plant Expression Vector pBI121

An aliquot of 1 μg of pETg1 was dissolved in 50 μl of H buffer, and 10 units of the restriction enzyme SalI (Takara Shuzo Co., Ltd.) was added. The reaction was carried out at 37° C. for 2 hours. After addition of 150 μl of ethanol, the reaction mixture was allowed to stand at −80° C. for 10 minutes, and then centrifuged at 10,000×g for 10 minutes. The obtained precipitate was washed with 200 μl of 70% ethanol, and dried under vacuum. The obtained DNA was dissolved in 50 μl of Klenow buffer, and one unit of Klenow fragment (Takara Shuzo Co., Ltd.) was added. The reaction was carried out at 30° C. for 30 minutes. After addition of 150 μl of ethanol, the reaction mixture was allowed to stand at −80° C. for 10 minutes, and then centrifuged at 10,000×g for 10 minutes. The obtained precipitate was washed with 200 μl of 70% ethanol, and dried under vacuum. The obtained DNA was dissolved in 50 μl of M buffer, and 10 units of the restriction enzyme SacI (Takara Shuzo Co., Ltd.) was added. The reaction was carried out at 37° C. for 2 hours. The reaction products were separated by electrophoresis through a 0.8% GTG agarose gel (Takara Shuzo Co., Ltd.), and a portion containing the inserted DNA fragment of about 2.2 kb was cut out. The DNA fragment was extracted and purified using the SUPREC™-01 (Takara Shuzo Co., Ltd.) according to the instructions provided by the manufacturer, and dissolved in 10 μl of TE buffer.

Separately, 1 μg of pEKa1 was dissolved in 50 μl of H buffer, and 10 units of the restriction enzyme SalI (Takara Shuzo Co., Ltd.) was added. The reaction was carried out at 37° C. for 2 hours. After addition of 150 μl of ethanol, the reaction mixture was allowed to stand at −80° C. for 10 minutes, and then centrifuged at 10,000×g for 10 minutes. The obtained precipitate was washed with 200 μl of 70% ethanol, and dried under vacuum. The obtained DNA was dissolved in 50 μl of Klenow buffer, and one unit of Klenow fragment (Takara Shuzo Co., Ltd.) was added. The reaction was carried out at 30° C. for 30 minutes. After addition of 150 μl of ethanol, the reaction mixture was allowed to stand at −80° C. for 10 minutes, and then centrifuged at 10,000×g for 10 minutes. The obtained precipitate was washed with 200 μl of 70% ethanol, and dried under vacuum. The obtained DNA was dissolved in 50 μl of M buffer, and 0.5 unit of the restriction enzyme SacI (Takara Shuzo Co., Ltd.) was added. The reaction was carried out at 37° C. for one hour. The reaction products were separated by electrophoresis through a 0.8% GTG agarose gel (Takara Shuzo Co., Ltd.), and a portion containing the inserted DNA fragment of about 1.9 kb was cut out. The DNA fragment was extracted and purified using the SUPREC™-01 (Takara Shuzo Co., Ltd.) according to the instructions provided by the manufacturer, and dissolved in 10 μl of TE buffer.

An aliquot of 1 μg of the plant expression vector pBI121 (GUS Gene Fusion System: Clonetech Co., Ltd.) was dissolved in 50 μl of Sma buffer [10 mM Tris hydrochloride buffer (pH 7.5), 10 mM magnesium chloride, 1 mM dithiothreitol, 20 mM potassium chloride], and 10 units of the restriction enzyme SmaI (Takara Shuzo Co., Ltd.) was added. The reaction was carried out at 30° C. for 2 hours. After addition of 150 μl of ethanol, the reaction mixture was allowed to stand at −80° C. for 10 minutes, and then centrifuged at 10,000×g for 10 minutes. The obtained precipitate was washed with 200 μl of 70% ethanol, and dried under vacuum. The obtained DNA was dissolved in 50 μl of M buffer, and 10 units of the restriction enzyme SacI (Takara Shuzo Co., Ltd.) was added. The reaction was carried out at 37° C. for 2 hours. The reaction products were separated by electrophoresis through a 0.8% GTG agarose gel (Takara Shuzo Co., Ltd.), and a portion containing the vector DNA fragment of about 11 kb was cut out. The vector DNA fragment was extracted and purified using the SUPREC™-01 (Takara Shuzo Co., Ltd.) according to the instructions provided by the manufacturer, and dissolved in 10 μl of TE buffer.

An aliquot of 1 μl of the TE buffer containing the vector DNA fragment and 1 μl of the TE buffer containing the DNA insert fragment of pETg1 were mixed, and ligation was carried out at 16° C. for 30 minutes using the DNA Ligation Kit (Takara Shuzo Co., Ltd.) according to the instructions provided by the manufacturer. The volume of the reaction mixture was 12 μl. Highly competent cells of E. coli JM109 (Toyobo Co., Ltd.) were transformed with 2 μl of the reaction mixture according to the instructions provided by the manufacturer. The transformed cells were cultured at 37° C. for 20 hours on kanamycin LB agar medium [1% Bacto Tryptone (Difco Laboratories), 0.5% Bacto Yeast Extract (Difco Laboratories), 1% sodium chloride, 50 μg/ml kanamycin, 1.5% Bacto Agar (Difco Laboratories)] according to the method described in the book by Maniatis et al. One of the formed colonies was isolated and cultured, and plasmid DNA was extracted and purified. The obtained plasmid was named pBTg1. pBTg1 is a plasmid composed of the plant expression vector pBI121, and inserted therein, Tg1, which is the AK14 homologous cDNA sequence derived form Russell prairie gentian.

An aliquot of 1 μl of the TE buffer containing the vector DNA fragment and 1 μl of the TE buffer containing the inserted DNA fragment of pEKa1 were mixed, and ligation was carried out at 16° C. for 30 minutes using the DNA Ligation Kit (Takara Shuzo Co., Ltd.) according to the instructions provided by the manufacturer. The volume of the reaction mixture was 12 μl. Highly competent cells of E. coli JM109 (Toyobo Co., Ltd.) were transformed with 2 μl of the reaction mixture according to the instructions provided by the manufacturer. The transformed cells were cultured at 37° C. for 20 hours on kanamycin LB agar medium [1% Bacto Tryptone (Difco Laboratories), 0.5% Bacto Yeast Extract (Difco Laboratories), 1% sodium chloride, 50 μg/ml kanamycin, 1.5% Bacto Agar (Difco Laboratories)] according to the method described in the book by Maniatis et al. One of the formed colonies was isolated and cultured, and plasmid DNA was extracted and purified. The obtained plasmid was named pBKa1. pBKa1 is a plasmid composed of the plant expression vector pBI121, and inserted therein, Ka1, which is the AK14 homologous cDNA sequence derived from campanula.

(2) Introduction of pBTg1 and pBKa1 into *Agrobacterium tumefaciens* LBA4404 Strain The plasmids pBTg1 and pBKa1 were respectively introduced into *Agrobacterium tumefaciens* LBA4404 strain using the triparental mating technique described in Example 5 (4).

EXAMPLE 14

Introduction of Tg1 and Ka1 into Tobacco and Their Expression (1) Introduction into Tobacco Using a Microorganism of the Genus Agrobacterium Leaves of tobacco (*Nicotiana tabacum* cv. petit Havana SR-1) were infected with each of the two types of Agrobacterium strains prepared in Example 13 (2) according to a method similar to that described in Example 6 (1) to obtain kanamycin-resistant transgenic tobacco.

(2) Detection of Enzyme Activity in Leaves of Transgenic Tobacco

Microsome fractions were prepared from 20 g each of the leaves of two types of transgenic tobacco obtained as above according to the method described in Example 2 (3), and flavonoid-3',5'-hydroxylase activity in the fractions was determined. As a result, said enzyme activity, which catalyzes the conversion of dihydroquercetin to dihydromyricetin, was detected in the microsome fractions of both transgenic tobacco. On the other hand, said enzyme activity was not detected in the microsome fraction prepared from leaves of the non-transgenic tobacco.

(3) Change in Pigments in Petals of the Transgenic Tobacco

Anthocyanidins were prepared from petals of the transgenic and non-transgenic tobacco plants, respectively, according to the method described in Example 2 (1), and analyzed. As a result, only cyanidin was detected in the non-transgenic tobacco, whereas cyanidin and delphinidin were detected in almost the same amounts in both the transgenic tobacco plants.

The flower colors were compared with The Japan Color Standard For Horticultural Plants (Japan Color Research Institute). The color of flowers of the transgenic tobacco corresponded to Color No. 8904 or 8905, and that of the non-transgenic tobacco corresponded to Color No. 9503 or 9504. That is, flowers of the transgenic tobacco showed more bluish color.

Industrial Applicability

According to the present invention, a plant having a pigment pattern which flowers or fruits of the plant do not originally have can be provided.

---

What is claimed is:

1. An isolated DNA encoding a polypeptide which has flavonoid-3',5'-hydroxylase activity, said DNA having a nucleotide sequence which encodes an amino acid sequence shown by any of SEQ ID NO: 66 or 67.

2. An isolated DNA according to claim 1, which has a nucleotide sequence according to SEQ ID NO: 63 or 64.

3. A recombinant DNA comprising a vector DNA having inserted therein the DNA of claim 1 or claim 2.

4. A plant or plant cell, which comprises the recombinant DNA according to claim 3.

5. The plant or plant cell according to claim 4, wherein said plant belongs to the genus Rosa, Nicotiana, Petunia or Dianthus.

6. A method for producing a plant or plant cell, which comprises the steps of:

introducing into a plant or plant cell a recombinant DNA comprising a vector DNA and a DNA which encodes a polypeptide having flavonoid-3',5' hydroxylase activity, said DNA having a nucleotide sequence which encodes an amino acid sequence shown by any of SEQ ID NO: 66 or 67;

expressing said DNA encoding a polypeptide having flavonoid-3',5'-hydroxylase activity; and harvesting said plant or plant cell thus obtained.

7. A method for producing a plant or plant cell, which comprises the steps of:

introducing into a plant or plant cell a recombinant DNA comprising a vector DNA and a DNA encoding a polypeptide having flavonoid-3',5'-hydroxylase activity, said polypeptide-encoding DNA comprising a nucleotide sequence according to SEQ ID NO: 63 or 64;

expressing said DNA encoding said polypeptide having flavonoid-3',5'-hydroxylase activity; and harvesting said plant or plant cell thus obtained.

8. A plant or plant cell, obtained by the method according to claim 7.

* * * * *

UNITED STATES PATENT AND TRADEMARK OFFICE
CERTIFICATE OF CORRECTION

PATENT NO.    : 6,114,601
DATED         : September 5, 2000
INVENTOR(S)   : Yasuhiro Kikuchi, et al.

It is certified that error appears in the above-identified patent and that said Letters Patent is hereby corrected as shown below:

ON THE TITLE PAGE:

[63] Related U.S. Application Data

"Continuation of application No. 08295,746, filed as application No. PCT/JP92/01520, No. 20, 1992, abandoned." should read --Continuation of application No. 08/295,746, filed Aug. 30, 1994, now abandoned, which is a 371 of PCTJP92/01520, filed Nov. 20, 1992.--; and

[56] References Cited, under OTHER PUBLICATIONS

After "Stevenson, T.W. (Dennis et al., eds)." Close up right margin.

Column 1:
Line 29, "genus," should read --genera,--.

Column 3:
Line 54, "a t" should read --at--.

Column 4:
Line 26, "tion (PRC)SSP.PCR" should read --tion (PRC). SSP.PCR--.

UNITED STATES PATENT AND TRADEMARK OFFICE
CERTIFICATE OF CORRECTION

PATENT NO.   : 6,114,601
DATED        : September 5, 2000
INVENTOR(S)  : Yasuhiro Kikuchi, et al.

It is certified that error appears in the above-identified patent and that said Letters Patent is hereby corrected as shown below:

Column 17:
Line 62, "after" should read --after being--.

Column 22:
Line 13, "of · about" should read --of about--.

Column 24:
Line 39, "form" should read --from--.

Column 25:
Line 20, "both" should read --both types of--.

Signed and Sealed this

Twelfth Day of June, 2001

*Attest:*

*Nicholas P. Godici*

*Attesting Officer*

NICHOLAS P. GODICI
*Acting Director of the United States Patent and Trademark Office*

SEQUENCE LISTING (1) GENERAL INFORMATION:

(iii) NUMBER OF SEQUENCES: 67

(2) INFORMATION FOR SEQ ID NO:1:

(i) SEQUENCE CHARACTERISTICS:
      (A) LENGTH: 1824 base pairs
      (B) TYPE: nucleic acid
      (C) STRANDEDNESS: double
      (D) TOPOLOGY: linear (ii) MOLECULE TYPE:cDNA to mRNA (vi) ORIGINAL SOURCE:
      (A) ORGANISM: Petunia hybrida
      (B) STRAIN: Falcon Blue (ix) FEATURE:
      (A) NAME/KEY: CDS
      (B) LOCATION: 116 to 1633
      (C) IDENTIFICATION METHOD:by experiment (xi) SEQUENCE DESCRIPTION: SEQ ID NO:1:

```
GCTACTTCGT TATATATATG TAAAATTGTG ACTTTGAAAA TCATTTAAAT TATCATAAGG        60

TTCATTTTAT CTTGATCAAA ATATTTACTT CGGCCATATA CGTTTTCCTT TAGTC ATG       118
                                                              Met
                                                               1

ATG CTA CTT ACT GAG CTT GGT GCA GCA ACT TCA ATC TTT CTA ATA GCA       166
Met Leu Leu Thr Glu Leu Gly Ala Ala Thr Ser Ile Phe Leu Ile Ala
          5                  10                  15

CAC ATA ATC ATT TCA ACT CTT ATT TCA AAA ACT ACC GGC CGG CAT CTA       214
His Ile Ile Ile Ser Thr Leu Ile Ser Lys Thr Thr Gly Arg His Leu
             20                  25                  30

CCG CCG GGG CCA AGA GGG TGG CCG GTG ATC GGA GCA CTT CCA CTT TTA       262
Pro Pro Gly Pro Arg Gly Trp Pro Val Ile Gly Ala Leu Pro Leu Leu
     35                  40                  45

GGA GCC ATG CCA CAT GTT TCC TTA GCT AAA ATG GCA AAA AAA TAT GGA       310
Gly Ala Met Pro His Val Ser Leu Ala Lys Met Ala Lys Lys Tyr Gly
```

```
                -continued 50                    55                    60                    65
GCA ATC ATG TAT CTC AAA GTT GGA ACA TGT GGC ATG GCA GTT GCT TCT           358
Ala Ile Met Tyr Leu Lys Val Gly Thr Cys Gly Met Ala Val Ala Ser
                70                    75                    80

ACC CCT GAT GCT GCT AAA GCA TTC TTG AAA ACA CTT GAT ATC AAC TTC           406
Thr Pro Asp Ala Ala Lys Ala Phe Leu Lys Thr Leu Asp Ile Asn Phe
            85                    90                    95

TCC AAT CGT CCA CCT AAT GCA GGT GCC ACT CAC TTA GCT TAT AAT GCT           454
Ser Asn Arg Pro Pro Asn Ala Gly Ala Thr His Leu Ala Tyr Asn Ala
        100                   105                   110

CAA GAC ATG GTT TTT GCA CAT TAT GGA CCA CGA TGG AAG TTG CTA AGG           502
Gln Asp Met Val Phe Ala His Tyr Gly Pro Arg Trp Lys Leu Leu Arg
    115                   120                   125

AAA TTA AGC AAC TTG CAT ATG CTA GGG GGA AAA GCC TTA GAG AAT TGG           550
Lys Leu Ser Asn Leu His Met Leu Gly Gly Lys Ala Leu Glu Asn Trp
130                   135                   140                   145

GCA AAT GTT CGT GCC AAT GAG CTA GGG CAC ATG CTA AAA TCA ATG TCC           598
Ala Asn Val Arg Ala Asn Glu Leu Gly His Met Leu Lys Ser Met Ser
                150                   155                   160

GAT ATG AGT CGA GAG GGC CAG AGG GTT GTG GTG GCG GAG ATG TTG ACA           646
Asp Met Ser Arg Glu Gly Gln Arg Val Val Val Ala Glu Met Leu Thr
            165                   170                   175

TTT GCC ATG GCC AAT ATG ATC GGA CAA GTG ATG CTA AGC AAA AGA GTA           694
Phe Ala Met Ala Asn Met Ile Gly Gln Val Met Leu Ser Lys Arg Val
        180                   185                   190

TTT GTA GAT AAA GGT GTT GAG GTA AAT GAA TTT AAG GAC ATG GTT GTA           742
Phe Val Asp Lys Gly Val Glu Val Asn Glu Phe Lys Asp Met Val Val
    195                   200                   205

GAG TTA ATG ACA ATA GCA GGG TAT TTC AAC ATT GGT GAT TTT ATT CCT           790
Glu Leu Met Thr Ile Ala Gly Tyr Phe Asn Ile Gly Asp Phe Ile Pro
210                   215                   220                   225

TGT TTA GCT TGG ATG GAT TTA CAA GGG ATA GAA AAA CGA ATG AAA CGT           838
Cys Leu Ala Trp Met Asp Leu Gln Gly Ile Glu Lys Arg Met Lys Arg
                230                   235                   240

TTA CAT AAG AAG TTT GAT GCT TTA TTG ACA AAG ATG TTT GAT GAA CAC           886
Leu His Lys Lys Phe Asp Ala Leu Leu Thr Lys Met Phe Asp Glu His
            245                   250                   255

AAA GCA ACT ACC TAT GAA CGT AAG GGG AAA CCA GAT TTT CTT GAT GTT           934
Lys Ala Thr Thr Tyr Glu Arg Lys Gly Lys Pro Asp Phe Leu Asp Val
        260                   265                   270

GTT ATG GAA AAT GGG GAC AAT TCT GAA GGA GAA AGA CTC AGT ACA ACC           982
Val Met Glu Asn Gly Asp Asn Ser Glu Gly Glu Arg Leu Ser Thr Thr
    275                   280                   285

AAC ATC AAA GCA CTT TTG CTG AAT TTG TTC ACA GCT GGT ACG GAC ACT          1030
Asn Ile Lys Ala Leu Leu Leu Asn Leu Phe Thr Ala Gly Thr Asp Thr
290                   295                   300                   305

TCT TCT AGT GCA ATA GAA TGG GCA CTT GCA GAA ATG ATG AAG AAC CCT          1078
Ser Ser Ser Ala Ile Glu Trp Ala Leu Ala Glu Met Met Lys Asn Pro
                310                   315                   320

GCC ATT TTG AAA AAA GCA CAA GCA GAA ATG GAT CAA GTC ATT GGA AGA          1126
Ala Ile Leu Lys Lys Ala Gln Ala Glu Met Asp Gln Val Ile Gly Arg
            325                   330                   335

AAT AGG CGT TTA CTC GAA TCC GAT ATC CCA AAT CTC CCT TAC CTC CGA          1174
Asn Arg Arg Leu Leu Glu Ser Asp Ile Pro Asn Leu Pro Tyr Leu Arg
        340                   345                   350

GCA ATT TGC AAA GAA ACA TTT CGA AAA CAC CCT TCT ACA CCA TTA AAT          1222
Ala Ile Cys Lys Glu Thr Phe Arg Lys His Pro Ser Thr Pro Leu Asn
    355                   360                   365

CTT CCT AGG ATC TCG AAC GAA CCA TGC ATA GTC GAT GGT TAT TAC ATA          1270
```

-continued

```
Leu Pro Arg Ile Ser Asn Glu Pro Cys Ile Val Asp Gly Tyr Tyr Ile
370                 375                 380                 385

CCA AAA AAC ACT AGG CTT AGT GTT AAC ATA TGG GCA ATT GGA AGA GAT     1318
Pro Lys Asn Thr Arg Leu Ser Val Asn Ile Trp Ala Ile Gly Arg Asp
            390                 395                 400

CCC CAA GTT TGG GAA AAT CCA CTA GAG TTT AAT CCC GAA AGA TTC TTG     1366
Pro Gln Val Trp Glu Asn Pro Leu Glu Phe Asn Pro Glu Arg Phe Leu
            405                 410                 415

AGT GGA AGA AAC TCC AAG ATT GAT CCT CGA GGG AAC GAT TTT GAA TTG     1414
Ser Gly Arg Asn Ser Lys Ile Asp Pro Arg Gly Asn Asp Phe Glu Leu
            420                 425                 430

ATA CCA TTT GGT GCT GGA CGA AGA ATT TGT GCA GGA ACA AGA ATG GGA     1462
Ile Pro Phe Gly Ala Gly Arg Arg Ile Cys Ala Gly Thr Arg Met Gly
435                 440                 445

ATT GTA ATG GTG GAA TAT ATA TTA GGA ACT TTG GTT CAT TCA TTT GAT     1510
Ile Val Met Val Glu Tyr Ile Leu Gly Thr Leu Val His Ser Phe Asp
450                 455                 460                 465

TGG AAA TTA CCA AGT GAA GTT ATT GAG TTG AAT ATG GAA GAA GCT TTT     1558
Trp Lys Leu Pro Ser Glu Val Ile Glu Leu Asn Met Glu Glu Ala Phe
            470                 475                 480

GGC TTA GCT TTG CAG AAA GCT GTC CCT CTT GAA GCT ATG GTT ACT CCA     1606
Gly Leu Ala Leu Gln Lys Ala Val Pro Leu Glu Ala Met Val Thr Pro
            485                 490                 495

AGG TTA CAA TTG GAT GTT TAT GTA CCA TAGCTATAGA TGTGTATTGT           1653
Arg Leu Gln Leu Asp Val Tyr Val Pro
            500                 505

GCTATAATTG CGCATGTTGT TGGTTGTAGC ATGAGATATT AAAAGGAGTA CATGAAGCGC   1713

ATTGCATGAG TTTAACTTGT AGCTCCTTAA TATTTTAGGT ATTTTTCAAT TAATAAGTTC   1773

TTGTTGGTTG GGTAAAAAAA AAAAAAAAAA AAAAAAAAA AAAAAAAAA A             1824

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:2:

TCGAATTCTN CCATTCGG                                                 18

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:3:

TCGAATTCTN CCATTTGG                                                 18

(2) INFORMATION FOR SEQ ID NO:4:

(i) SEQUENCE CHARACTERISTICS:
        (A) LENGTH: 18 base pairs
        (B) TYPE: nucleic acid
```

```
            (C) STRANDEDNESS: single
            (D) TOPOLOGY: linear (ii) MOLECULE TYPE:Other nucleic acid
            (A) DESCRIPTION: Synthetic DNA (xi) SEQUENCE DESCRIPTION: SEQ ID NO: 4:

TCGAATTCTN CCCTTCGG                                                      18

(2) INFORMATION FOR SEQ ID NO:5:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE:Other nucleic acid
            (A) DESCRIPTION: Synthetic DNA (xi) SEQUENCE DESCRIPTION: SEQ ID NO:5:

TCGAATTCTN CCCTTTGG                                                      18

(2) INFORMATION FOR SEQ ID NO:6:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE:Other nucleic acid
            (A) DESCRIPTION: Synthetic DNA (xi) SEQUENCE DESCRIPTION: SEQ ID NO:6:

TCGAATTCTN CCGTTCGG                                                      18

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE:Other nucleic acid
            (A) DESCRIPTION: Synthetic DNA (xi) SEQUENCE DESCRIPTION: SEQ ID NO: 7:

TCGAATTCTN CCGTTTGG                                                      18

(2) INFORMATION FOR SEQ ID NO:8:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE:Other nucleic acid
            (A) DESCRIPTION: Synthetic DNA (xi) SEQUENCE DESCRIPTION: SEQ ID NO:8:

TCGAATTCTN CCTTTCGG                                                      18

(2) INFORMATION FOR SEQ ID NO:9:

(i) SEQUENCE CHARACTERISTICS:
            (A) LENGTH: 18 base pairs
```

```
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:9:

TCGAATTCTN CCTTTTGG                                                   18

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:10:

TCGAATTCTN CCATTCTC                                                   18

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:11:

TCGAATTCTN CCATTTTC                                                   18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE:Genomic DNA (xi) SEQUENCE DESCRIPTION: SEQ ID NO:12:

TCGAATTCTN CCCTTCTC                                                   18

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:13:

TCGAATTCTN CCCTTTTC                                                   18

(2) INFORMATION FOR SEQ ID NO:14:

(i) SEQUENCE CHARACTERISTICS:
        (A) LENGTH: 18 base pairs
```

(B) TYPE: nucleic acid
            (C) STRANDEDNESS: single
            (D) TOPOLOGY: linear (ii) MOLECULE TYPE:Other nucleic acid
            (A) DESCRIPTION: Synthetic DNA (xi) SEQUENCE DESCRIPTION: SEQ ID NO:14:

TCGAATTCTN CCGTTCTC                                                  18

(2) INFORMATION FOR SEQ ID NO:15:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE:Other nucleic acid
            (A) DESCRIPTION: Synthetic DNA (xi) SEQUENCE DESCRIPTION: SEQ ID NO:15:

TCGAATTCTN CCGTTTTC                                                  18

(2) INFORMATION FOR SEQ ID NO:16:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE:Other nucleic acid
            (A) DESCRIPTION: Synthetic DNA (xi) SEQUENCE DESCRIPTION: SEQ ID NO:16:

TCGAATTCTN CCTTTCTC                                                  18

(2) INFORMATION FOR SEQ ID NO:17:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE:Other nucleic acid
            (A) DESCRIPTION: Synthetic DNA (xi) SEQUENCE DESCRIPTION: SEQ ID NO:17:

TCGAATTCTN CCTTTTTC                                                  18

(2) INFORMATION FOR SEQ ID NO:18:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE:Other nucleic acid
            (A) DESCRIPTION: Synthetic DNA (xi) SEQUENCE DESCRIPTION: SEQ ID NO:18:

GCGGATCCCN CCNAAACA                                                  18

(2) INFORMATION FOR SEQ ID NO:19:

(i) SEQUENCE CHARACTERISTICS:

(A) LENGTH: 18 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:19:

GCGGATCCCN CCNAAGCA                                                18

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:20:

GCGGATCCCN CCNACACA                                                18

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:21:

GCGGATCCCN CCNACGCA                                                18

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:22:

GCGGATCCCN CCNAGACA                                                18

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:23:

GCGGATCCCN CCNAGGCA                                                18

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:24:

GCGGATCCCN CCNATACA                                                    18

(2) INFORMATION FOR SEQ ID NO:25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:25:

GCGGATCCCN CCNATGCA                                                    18

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:26:

GCGGATCCTN CCNGGACA                                                    18

(2) INFORMATION FOR SEQ ID NO:27:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:27:

GCGGATCCTN CCNGGGCA                                                    18

(2) INFORMATION FOR SEQ ID NO:28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:28:

GCGGATCCCN CCNGCACA                                                    18

(2) INFORMATION FOR SEQ ID NO:29:

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:29:

GCGGATCCCN CCNGCGCA                                                        18

(2) INFORMATION FOR SEQ ID NO:30:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE:cDNA to mRNA (vi) ORIGINAL SOURCE:
        (A) ORGANISM: Petunia hybrida
        (B) STRAIN: Falcon Blue
        (F) TISSUE TYPE:flower limbs in the bud (xi) SEQUENCE DESCRIPTION: SEQ ID NO:30:

CCN TTT GGT AGT GGA AGG AGG ATT TGC CCN GG                                 32
Pro Phe Gly Ser Gly Arg Arg Ile Cys Pro Gly
1               5                   10

(2) INFORMATION FOR SEQ ID NO:31:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE:cDNA to mRNA (vi) ORIGINAL SOURCE:
        (A) ORGANISM: Petunia hybrida
        (B) STRAIN: Falcon Blue
        (F) TISSUE TYPE:flower limbs in the bud (xi) SEQUENCE DESCRIPTION: SEQ ID NO:31:

CCN TTT GGT GCT GGA AGA CGT ATA TGT CCN GG                                 32
Pro Phe Gly Ala Gly Arg Arg Ile Cys Pro Gly
1               5                   10

(2) INFORMATION FOR SEQ ID NO:32:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE:cDNA to mRNA (vi) ORIGINAL SOURCE:
        (A) ORGANISM: Petunia hybrida
        (B) STRAIN: Falcon Blue
        (F) TISSUE TYPE:flower limbs in the bud (xi) SEQUENCE DESCRIPTION: SEQ ID NO:32:

CCN TTT GGT GCT GGT CGA AGA ATA TGC CCN GG                                 32
Pro Phe Gly Ala Gly Arg Arg Ile Cys Pro Gly
1               5                   10
```

(2) INFORMATION FOR SEQ ID NO:33:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE:cDNA to mRNA (vi) ORIGINAL SOURCE:
        (A) ORGANISM: Petunia hybrida
        (B) STRAIN: Falcon Blue
        (F) TISSUE TYPE:flower limbs in the bud (xi) SEQUENCE DESCRIPTION: SEQ ID NO:33:

```
CCN TTT GGG ACT GGT CGA CGA ATT TGT CCN GG                              32
Pro Phe Gly Thr Gly Arg Arg Ile Cys Pro Gly
1               5                   10
```

(2) INFORMATION FOR SEQ ID NO:34:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE:cDNA to mRNA (vi) ORIGINAL SOURCE:
        (A) ORGANISM: Petunia hybrida
        (B) STRAIN: Falcon Blue
        (F) TISSUE TYPE:flower limbs in the bud (xi) SEQUENCE DESCRIPTION: SEQ ID NO:34:

```
CCN TTT GGC TCG GGA AGA CGA TCT TGT CCN GG                              32
Pro Phe Gly Ser Gly Arg Arg Ser Cys Pro Gly
1               5                   10
```

(2) INFORMATION FOR SEQ ID NO:35:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE:cDNA to mRNA (vi) ORIGINAL SOURCE:
        (A) ORGANISM: Petunia hybrida
        (B) STRAIN: Falcon Blue
        (F) TISSUE TYPE:flower limbs in the bud (xi) SEQUENCE DESCRIPTION: SEQ ID NO:35:

```
CCN TTT GGT GCT GGT AGA AGA GTG TGT CCN GG                              32
Pro Phe Gly Ala Gly Arg Arg Val Cys Pro Gly
1               5                   10
```

(2) INFORMATION FOR SEQ ID NO:36:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE:cDNA to mRNA (vi) ORIGINAL SOURCE:

```
        (A) ORGANISM: Petunia hybrida
        (B) STRAIN: Falcon Blue
        (F) TISSUE TYPE:flower limbs in the bud (xi) SEQUENCE DESCRIPTION: SEQ ID NO:36:

CCN TTT GGA GTA GGC CTA AGA ATG TGC CCN GG                          32
Pro Phe Gly Val Gly Leu Arg Met Cys Pro Gly
1               5                   10

(2) INFORMATION FOR SEQ ID NO:37:

(i) SEQUENCE CHARACTERISTICS:
          (A) LENGTH: 32 base pairs
          (B) TYPE: nucleic acid
          (C) STRANDEDNESS: double
          (D) TOPOLOGY: linear (ii) MOLECULE TYPE:cDNA to mRNA (vi) ORIGINAL SOURCE:
          (A) ORGANISM: Petunia hybrida
          (B) STRAIN: Falcon Blue
          (F) TISSUE TYPE:flower limbs in the bud (xi) SEQUENCE DESCRIPTION: SEQ ID NO:37:

CCN TTT GGT GGA GGA CCA CGG CGA TGT CCN GG                          32
Pro Phe Gly Gly Gly Pro Arg Arg Cys Pro Gly
1               5                   10

(2) INFORMATION FOR SEQ ID NO:38:

(i) SEQUENCE CHARACTERISTICS:
          (A) LENGTH: 32 base pairs
          (B) TYPE: nucleic acid
          (C) STRANDEDNESS: double
          (D) TOPOLOGY: linear (ii) MOLECULE TYPE:cDNA to mRNA (vi) ORIGINAL SOURCE:
          (A) ORGANISM: Petunia hybrida
          (B) STRAIN: Falcon Blue
          (F) TISSUE TYPE:flower limbs in the bud (xi) SEQUENCE DESCRIPTION: SEQ ID NO:38:

CCN TTT GGT GTT GGT AGG AGG AGT TGC CCN GG                          32
Pro Phe Gly Val Gly Arg Arg Ser Cys Pro Gly
1               5                   10

(2) INFORMATION FOR SEQ ID NO:39:

(i) SEQUENCE CHARACTERISTICS:
          (A) LENGTH: 32 base pairs
          (B) TYPE: nucleic acid
          (C) STRANDEDNESS: double
          (D) TOPOLOGY: linear (ii) MOLECULE TYPE:cDNA to mRNA (vi) ORIGINAL SOURCE:
          (A) ORGANISM: Petunia hybrida
          (B) STRAIN: Falcon Blue
          (F) TISSUE TYPE:flower limbs in thew bud (xi) SEQUENCE DESCRIPTION: SEQ ID NO:39:

CCN TTC GGA GTC GGC CCC AAA ATG TGC CCN GG                          32
Pro Phe Gly Val Gly Pro Lys Met Cys Pro Gly
1               5                   10

(2) INFORMATION FOR SEQ ID NO:40:
```

```
    (i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE:cDNA to mRNA (vi) ORIGINAL SOURCE:
        (A) ORGANISM: Petunia hybrida
        (B) STRAIN: Falcon Blue
        (F) TISSUE TYPE:flower limbs in the bud (xi) SEQUENCE DESCRIPTION: SEQ ID NO:40:

CCN TTC GGT GGA GGA CCA AGA AAA TGC GTN GG                              32
Pro Phe Gly Gly Gly Pro Arg Lys Cys Val Gly
1               5                   10

(2) INFORMATION FOR SEQ ID NO:41:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE:cDNA to mRNA (vi) ORIGINAL SOURCE:
        (A) ORGANISM: Petunia hybrida
        (B) STRAIN: Falcon Blue
        (F) TISSUE TYPE:flower limbs in the bud (xi) SEQUENCE DESCRIPTION: SEQ ID NO:41:

CCN TTC GGC TTT GGT CCT CGA AAA TGC GTN GG                              32
Pro Phe Gly Phe Gly Pro Arg Lys Cys Val Gly
1               5                   10

(2) INFORMATION FOR SEQ ID NO:42:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE:cDNA to mRNA (vi) ORIGINAL SOURCE:
        (A) ORGANISM: Petunia hybrida
        (B) STRAIN: Falcon Blue
        (F) TISSUE TYPE:flower limbs in the bud (xi) SEQUENCE DESCRIPTION: SEQ ID NO:42:

CCN TTT GGC AGT GGT TTC TGT TCA TGT CCN GG                              32
Pro Phe Gly Ser Gly Phe Cys Ser Cys Pro Gly
1               5                   10

(2) INFORMATION FOR SEQ ID NO:43:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE:cDNA to mRNA (iii) HYPOTHETICAL:

(iv) ANTI-SENSE:

(vi) ORIGINAL SOURCE:
```

```
        (A) ORGANISM: Petunia hybrida
        (B) STRAIN: Falcon Blue
        (F) TISSUE TYPE:flower limbs in the bud (xi) SEQUENCE DESCRIPTION: SEQ ID NO:43:

CCN TTT GGT GCT GGA CGA AGA ATT TGT GCN GG                              32
Pro Phe Gly Ala Gly Arg Arg Ile Cys Ala Gly
1               5                   10

(2) INFORMATION FOR SEQ ID NO:44:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE:cDNA to mRNA (vi) ORIGINAL SOURCE:
        (A) ORGANISM: Petunia hybrida
        (B) STRAIN: Falcon Blue
        (F) TISSUE TYPE:flower limbs in the bud (xi) SEQUENCE DESCRIPTION: SEQ ID NO:44:

CCN TTT GGT GGT GGA AGA AGG ATA TGT CCN GG                              32
Pro Phe Gly Gly Gly Arg Arg Ile Cys Pro Gly
1               5                   10

(2) INFORMATION FOR SEQ ID NO:45:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:45:

CCNGGGCAAA TCCTCCT                                                      17

(2) INFORMATION FOR SEQ ID NO:46:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:46:

CCNGGACATA TACGTCT                                                      17

(2) INFORMATION FOR SEQ ID NO:47:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:47:

CCNGGGCATA TTCTTCG                                                      17
```

(2) INFORMATION FOR SEQ ID NO:48:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:48:

CCNGGACAAA TTCGTCG                                        17

(2) INFORMATION FOR SEQ ID NO:49:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:49:

CCNGGACAAG ATCGTCT                                        17

(2) INFORMATION FOR SEQ ID NO:50:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:50:

CCNGGACACA CTCTTCT                                        17

(2) INFORMATION FOR SEQ ID NO:51:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:51:

CCNGGGCACA TTCTTAG                                        17

(2) INFORMATION FOR SEQ ID NO:52:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:52:

```
CCNGGACATC GCCGTGG                                                    17
```

(2) INFORMATION FOR SEQ ID NO:53:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:53:

```
CCNGGGCAAC TCCTCCT                                                    17
```

(2) INFORMATION FOR SEQ ID NO:54:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:54:

```
CCNGGGCACA TTTTGGG                                                    17
```

(2) INFORMATION FOR SEQ ID NO:55:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:55:

```
CCNACGCATT TTCTTGG                                                    17
```

(2) INFORMATION FOR SEQ ID NO:56:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:56:

```
CCNACACATT TTCGAGG                                                    17
```

(2) INFORMATION FOR SEQ ID NO:57:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:57:

```
CCNGGACATG AACAGAA                                                    17

(2) INFORMATION FOR SEQ ID NO:58:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:58:

CCNGCACAAA TTCTTCG                                                    17

(2) INFORMATION FOR SEQ ID NO:59:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:59:

CCNGGACATA TCCTTCT                                                    17

(2) INFORMATION FOR SEQ ID NO:60:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:60:

TGATCCGGAA TTCGTGCCAT CAAG                                            24

(2) INFORMATION FOR SEQ ID NO:61:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA (xi) SEQUENCE DESCRIPTION: SEQ ID NO:61:

CGCTTGATGG CACGAATTCC GGATCA                                          26

(2) INFORMATION FOR SEQ ID NO:62:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE:Other nucleic acid
        (A) DESCRIPTION: Synthetic DNA
```

-continued (xi) SEQUENCE DESCRIPTION: SEQ ID NO:62:

```
CCNTTTGGTG CTGGA                                                    15
```

(2) INFORMATION FOR SEQ ID NO:63:

(i) SEQUENCE CHARACTERISTICS:
        (A) LENGTH: 2174 base pairs
        (B) TYPE: nucleic acid
        (C) STRANDEDNESS: double
        (D) TOPOLOGY: linear (ii) MOLECULE TYPE:cDNA to mRNA (vi) ORIGINAL SOURCE:
        (A) ORGANISM: Eustoma russellianum (ix) FEATURE:
        (A) NAME/KEY: CDS
        (B) LOCATION: 92 to 1621
        (C) IDENTIFICATION METHOD:by experiment (xi) SEQUENCE DESCRIPTION: SEQ ID NO:63:

```
GAAAACTATC CATTCTTACC AAGATAAGCA CATTTCTCGT TTCTTTCTAA GAAGAGCATT        60

AGGCCAATTC TTTAAGCCCG TACTTAACGA T ATG GCT GTT GGA AAT GGC GTT         112
                                  Met Ala Val Gly Asn Gly Val
                                   1               5

TTA CTT CAC ATT GCT GCA TCA TTG ATG CTG TTC TTT CAT GTG CAA AAA        160
Leu Leu His Ile Ala Ala Ser Leu Met Leu Phe Phe His Val Gln Lys
         10                  15                  20

CTT GTG CAA TAT CTA TGG ATG AAT TCC AGG CGC CAC CGG CTT CCA CCT        208
Leu Val Gln Tyr Leu Trp Met Asn Ser Arg Arg His Arg Leu Pro Pro
     25                  30                  35

GGC CCG ATA GGG TGG CCG GTT CTC GGT GCC CTT CGG CTT TTA GGC ACC        256
Gly Pro Ile Gly Trp Pro Val Leu Gly Ala Leu Arg Leu Leu Gly Thr
 40                  45                  50                  55

ATG CCT CAT GTT GCA CTA GCT AAC ATG GCC AAA AAA TAT GGT CCT GTT        304
Met Pro His Val Ala Leu Ala Asn Met Ala Lys Lys Tyr Gly Pro Val
                 60                  65                  70

ATG TAC TTA AAG GTA GGC AGC TGT GGT CTG GCC GTG GCA TCG ACT CCT        352
Met Tyr Leu Lys Val Gly Ser Cys Gly Leu Ala Val Ala Ser Thr Pro
             75                  80                  85

GAG GCT GCT AAG GCA TTC CTC AAA ACA CTT GAC ATG AAC TTC TCG AAT        400
Glu Ala Ala Lys Ala Phe Leu Lys Thr Leu Asp Met Asn Phe Ser Asn
         90                  95                 100

CGG CCG CCT AAT GCA GGG GCT ACC CAT TTG GCC TAT AAT GCT CAG GAC        448
Arg Pro Pro Asn Ala Gly Ala Thr His Leu Ala Tyr Asn Ala Gln Asp
    105                 110                 115

ATG GTG TTT GCA GAC TAT GGT CCC AGA TGG AAG CTG CTA CGT AAA CTC        496
Met Val Phe Ala Asp Tyr Gly Pro Arg Trp Lys Leu Leu Arg Lys Leu
120                 125                 130                 135

AGC AAC ATA CAC ATT CTT GGT GGC AAG GCC CTG CAG GGC TGG GAA GAA        544
Ser Asn Ile His Ile Leu Gly Gly Lys Ala Leu Gln Gly Trp Glu Glu
                140                 145                 150

GTT CGA AAG AAA GAG CTT GGG TAT ATG CTC TAT GCA ATG GCT GAA TCA        592
Val Arg Lys Lys Glu Leu Gly Tyr Met Leu Tyr Ala Met Ala Glu Ser
            155                 160                 165

GGG CGA CAT GGC CAG CCA GTG GTG GTG TCA GAG ATG CTA ACA TAT GCC        640
Gly Arg His Gly Gln Pro Val Val Val Ser Glu Met Leu Thr Tyr Ala
        170                 175                 180

ATG GCA AAC ATG TTA GGC CAA GTG ATG CTC AGC AAG CGA GTT TTC GGG        688
Met Ala Asn Met Leu Gly Gln Val Met Leu Ser Lys Arg Val Phe Gly
    185                 190                 195
```

```
TCT CAA GGA TCA GAA TCC AAT GAG TTC AAA GAT ATG GTG GTT GAG TTG         736
Ser Gln Gly Ser Glu Ser Asn Glu Phe Lys Asp Met Val Val Glu Leu
200             205                 210                 215

ATG ACT GTT GCT GGC TAT TTC AAC ATA GGT GAT TTT ATC CCC TCG ATT         784
Met Thr Val Ala Gly Tyr Phe Asn Ile Gly Asp Phe Ile Pro Ser Ile
                220                 225                 230

GCA TGG ATG GAT TTG CAG GGG ATT CAG GGC GGA ATG AAA CGG TTG CAT         832
Ala Trp Met Asp Leu Gln Gly Ile Gln Gly Gly Met Lys Arg Leu His
            235                 240                 245

AAG AAG TTT GAT GCT TTG TTG ACT CGG TTG CTG GAA GAG CAC ACT GCA         880
Lys Lys Phe Asp Ala Leu Leu Thr Arg Leu Leu Glu Glu His Thr Ala
        250                 255                 260

TCG GCT CAT GAG CGT AAA GGC AGC CCT GAT TTC CTT GAT TTT GTC GTT         928
Ser Ala His Glu Arg Lys Gly Ser Pro Asp Phe Leu Asp Phe Val Val
    265                 270                 275

GCA AAT GGC GAC AAT TCT GAA GGC GAA AGG CTT CAG ACA GTC AAT ATC         976
Ala Asn Gly Asp Asn Ser Glu Gly Glu Arg Leu Gln Thr Val Asn Ile
280                 285                 290                 295

AAG GCT CTT TTA TTG AAC ATG TTT ACC GCT GGT ACG GAT ACA TCT TCA        1024
Lys Ala Leu Leu Leu Asn Met Phe Thr Ala Gly Thr Asp Thr Ser Ser
                300                 305                 310

AGC GTC ATA GAG TGG GCG CTG GCC GAG TTG CTA AAG AAT CCA ATC ATC        1072
Ser Val Ile Glu Trp Ala Leu Ala Glu Leu Leu Lys Asn Pro Ile Ile
            315                 320                 325

CTA AGA CGA GCC CAA GAA GAA ATG GAC GGT GTG ATC GGC CGA GAC CGG        1120
Leu Arg Arg Ala Gln Glu Glu Met Asp Gly Val Ile Gly Arg Asp Arg
        330                 335                 340

CGG TTT CTT GAG GCA GAC ATA TCA AAG TTG CCA TAT CTC CAA GCC ATC        1168
Arg Phe Leu Glu Ala Asp Ile Ser Lys Leu Pro Tyr Leu Gln Ala Ile
    345                 350                 355

TGC AAA GAA GCT TTC AGA AAG CAT CCT TCC ACG CCT TTA AAT CTC CCA        1216
Cys Lys Glu Ala Phe Arg Lys His Pro Ser Thr Pro Leu Asn Leu Pro
360                 365                 370                 375

CGA ATC GCG TCG CAA GCA TGT GAA GTA AAT GGA CAC TAC ATA CCA AAG        1264
Arg Ile Ala Ser Gln Ala Cys Glu Val Asn Gly His Tyr Ile Pro Lys
                380                 385                 390

GGC ACT AGG CTC AGC GTT AAC ATA TGG GCT ATT GGA AGA GAT CCA TCT        1312
Gly Thr Arg Leu Ser Val Asn Ile Trp Ala Ile Gly Arg Asp Pro Ser
            395                 400                 405

GTG TGG GAA AAT CCA AAT GAA TTT AAC CCT GAT AGG TTT TTG GAA CGA        1360
Val Trp Glu Asn Pro Asn Glu Phe Asn Pro Asp Arg Phe Leu Glu Arg
        410                 415                 420

AAG AAT GCC AAG ATC GAT CCA CGA GGA AAT GAT TTT GAG CTG ATC CCA        1408
Lys Asn Ala Lys Ile Asp Pro Arg Gly Asn Asp Phe Glu Leu Ile Pro
    425                 430                 435

TTT GGA GCT GGA AGA AGA ATT TGC GCT GGA ACA AGA TTG GGA ATA CTT        1456
Phe Gly Ala Gly Arg Arg Ile Cys Ala Gly Thr Arg Leu Gly Ile Leu
440                 445                 450                 455

CTA GTG GAG TAT ATT TTG GGA ACT TTG GTG CAT TCT TTT GTT TGG GAA        1504
Leu Val Glu Tyr Ile Leu Gly Thr Leu Val His Ser Phe Val Trp Glu
                460                 465                 470

TTG CCA TCC TCT GTG ATT GAA CTT AAC ATG GAT GAG TCT TTT GGG CTT        1552
Leu Pro Ser Ser Val Ile Glu Leu Asn Met Asp Glu Ser Phe Gly Leu
            475                 480                 485

GCT CTG CAG AAG GCA GTG CCT CTT GCT GCT ATG GTC ACT CCA CGG CTG        1600
Ala Leu Gln Lys Ala Val Pro Leu Ala Ala Met Val Thr Pro Arg Leu
        490                 495                 500

CCT CTC CAT ATT TAC TCT CCT TGAGATCTGT GTTCTATGGG TCATTGAGAA           1651
Pro Leu His Ile Tyr Ser Pro
    505                 510
```

-continued

```
ACAACCGCTG TGTGTTTCTA ACACATGAAT ATGGTTGTGT ACATCTGGCT TATTTATACC    1711

TCCCTATAGA CGAGAAGCCT CGAAGGCAAT GGGGTAATGT TGTTGTTGTC GTGAGACATG    1771

TCTTCTATGT TTCTAAGCAG ATGAGATCTA AGTAGATGAC ATATGCTGTC TTCTACTATT    1831

TTGAAATTAG ATATGCCCCA GAATAAACGC ATCAAACTCG TAATTCGATA CAAAAAATTC    1891

TTGTTGTGGT TTTGAATAAA CACTTATAGA TAATTTGAGA TTTAGAATCG GGTATTTTGG    1951

TATATTTTCC ACGTTCATAG GAGTTCGTCC ATGTTTCTGA TTTACAAATA TGATTTTTTT    2011

TGGACATTTC TAATAATATC AATTTGTATT CCTGTTTTAA GTTTTTTAAT TTCTCAAGTT    2071

TTAGTCCTAA TTAGCAAAGG ACCAGAAAAA CTGTCTAGTT ATGAATCGGG GATAGAACCA    2131

GCAGGAGATG CTGGTTACAA TTTCGATTAA AAAAAAAAAA AAA                     2174
```

(2) INFORMATION FOR SEQ ID NO:64:

(i) SEQUENCE CHARACTERISTICS:
        (A) LENGTH: 1927 base pairs
        (B) TYPE: nucleic acid
        (C) STRANDEDNESS: double
        (D) TOPOLOGY: linear (ii) MOLECULE TYPE:cDNA to mRNA (vi) ORIGINAL SOURCE:
        (A) ORGANISM: Campanula medium (ix) FEATURE:
        (A) NAME/KEY: CDS
        (B) LOCATION: 180 to 1748
        (C) IDENTIFICATION METHOD:by experiment (xi) SEQUENCE DESCRIPTION: SEQ ID NO:64:

```
ACCAAATGAG CTTTGTAATT TGAGATTAAT CATAATTGCA TGCTCAACTA ACATTCTGTA      60

TTCATATATC CATATGTATT TTGACCTATA GATATTCAT TACACCTTGA GGCCTTTATA     120

TATAGAGAGT GTATCTACTT CCCTTAATAT CACCTTTTCA TTCAACAAGT GAAGCCACC     179

ATG TCT ATA GAC ATA TCC ACC CTC TTC TAT GAA CTT GTT GCA GCA ATT      227
Met Ser Ile Asp Ile Ser Thr Leu Phe Tyr Glu Leu Val Ala Ala Ile
  1               5                  10                  15

TCA CTC TAC TTA GCT ACC TAC TCT TTC ATT CGT TTC CTC TTC AAA CCC      275
Ser Leu Tyr Leu Ala Thr Tyr Ser Phe Ile Arg Phe Leu Phe Lys Pro
              20                  25                  30

TCT CAC CAC CAC CAC CTC CCT CCC GGC CCA ACC GGA TGG CCG ATC ATC      323
Ser His His His His Leu Pro Pro Gly Pro Thr Gly Trp Pro Ile Ile
          35                  40                  45

GGA GCC CTT CCA CTC TTA GGC ACC ATG CCA CAT GTT TCC TTA GCC GAC      371
Gly Ala Leu Pro Leu Leu Gly Thr Met Pro His Val Ser Leu Ala Asp
      50                  55                  60

ATG GCC GTT AAA TAC GGT CCT ATA ATG TAC CTA AAA CTT GGT TCA AAG      419
Met Ala Val Lys Tyr Gly Pro Ile Met Tyr Leu Lys Leu Gly Ser Lys
 65                  70                  75                  80

GGC ACC GTC GTG GCC TCA AAT CCA AAA GCC GCC CGA GCC TTC TTG AAA      467
Gly Thr Val Val Ala Ser Asn Pro Lys Ala Ala Arg Ala Phe Leu Lys
                  85                  90                  95

ACC CAT GAT GCC AAT TTT TCT AAC CGT CCG ATT GAT GGG GGC CCT ACC      515
Thr His Asp Ala Asn Phe Ser Asn Arg Pro Ile Asp Gly Gly Pro Thr
             100                 105                 110

TAC CTC GCG TAT AAT GCA CAA GAC ATG GTT TTT GCA GAA TAT GGC CCA      563
Tyr Leu Ala Tyr Asn Ala Gln Asp Met Val Phe Ala Glu Tyr Gly Pro
         115                 120                 125

AAA TGG AAG CTT TTG CGA AAG CTA TGT AGC TTG CAC ATG TTA GGC CCG      611
```

```
                Lys Trp Lys Leu Leu Arg Lys Leu Cys Ser Leu His Met Leu Gly Pro
                    130                 135                 140

AAG GCA CTC GAG GAT TGG GCT CAT GTC AAA GTT TCA GAG GTC GGT CAT            659
Lys Ala Leu Glu Asp Trp Ala His Val Lys Val Ser Glu Val Gly His
145                 150                 155                 160

ATG CTC AAA GAA ATG TAC GAG CAA TCG AGT AAG TCA GTG CCA GTG CCA            707
Met Leu Lys Glu Met Tyr Glu Gln Ser Ser Lys Ser Val Pro Val Pro
                165                 170                 175

GTG GTG GTG CCA GAG ATG TTA ACT TAT GCC ATG GCT AAT ATG ATT GGA            755
Val Val Val Pro Glu Met Leu Thr Tyr Ala Met Ala Asn Met Ile Gly
            180                 185                 190

CGA ATC ATA CTC AGC CGA CGC CCT TTT GTT ATC ACG AGC AAA TTA GAC            803
Arg Ile Ile Leu Ser Arg Arg Pro Phe Val Ile Thr Ser Lys Leu Asp
                195                 200                 205

TCG TCT GCT TCT GCT TCT GCT TCT GTT AGT GAA TTC CAA TAT ATG GTT            851
Ser Ser Ala Ser Ala Ser Ala Ser Val Ser Glu Phe Gln Tyr Met Val
            210                 215                 220

ATG GAG CTC ATG AGG ATG GCA GGG TTG TTC AAT ATT GGT GAT TTC ATA            899
Met Glu Leu Met Arg Met Ala Gly Leu Phe Asn Ile Gly Asp Phe Ile
225                 230                 235                 240

CCA TAT ATT GCA TGG ATG GAT TTG CAA GGC ATT CAA CGT GAT ATG AAG            947
Pro Tyr Ile Ala Trp Met Asp Leu Gln Gly Ile Gln Arg Asp Met Lys
                245                 250                 255

GTT ATA CAG AAA AAG TTT GAT GTC TTG TTG AAC AAA ATG ATC AAG GAA            995
Val Ile Gln Lys Lys Phe Asp Val Leu Leu Asn Lys Met Ile Lys Glu
            260                 265                 270

CAT ACA GAA TCC GCT CAT GAT CGC AAA GAT AAT CCT GAT TTT CTT GAT           1043
His Thr Glu Ser Ala His Asp Arg Lys Asp Asn Pro Asp Phe Leu Asp
                275                 280                 285

ATT CTT ATG GCG GCT ACC CAA GAA AAC ACG GAG GGA ATT CAG CTT AAT           1091
Ile Leu Met Ala Ala Thr Gln Glu Asn Thr Glu Gly Ile Gln Leu Asn
            290                 295                 300

CTT GTA AAT GTT AAG GCA CTT CTT TTG GAT TTA TTC ACG GCG GGC ACG           1139
Leu Val Asn Val Lys Ala Leu Leu Leu Asp Leu Phe Thr Ala Gly Thr
305                 310                 315                 320

GAT ACA TCA TCA AGT GTG ATC GAA TGG GCA CTA GCC GAA ATG TTG AAC           1187
Asp Thr Ser Ser Ser Val Ile Glu Trp Ala Leu Ala Glu Met Leu Asn
                325                 330                 335

CAT CGA CAG ATC CTA AAC CGG GCC CAC GAA GAA ATG GAC CAA GTC ATT           1235
His Arg Gln Ile Leu Asn Arg Ala His Glu Glu Met Asp Gln Val Ile
            340                 345                 350

GGC AGA AAC AGA AGA CTA GAA CAA TCT GAC ATA CCA AAC TTG CCA TAT           1283
Gly Arg Asn Arg Arg Leu Glu Gln Ser Asp Ile Pro Asn Leu Pro Tyr
                355                 360                 365

TTC CAA GCC ATA TGC AAA GAA ACA TTC CGA AAA CAC CCT TCC ACG CCC           1331
Phe Gln Ala Ile Cys Lys Glu Thr Phe Arg Lys His Pro Ser Thr Pro
            370                 375                 380

TTA AAC CTC CCA AGA ATC TCA ACA GAA GCA TGT GAA GTG GAC GGA TTT           1379
Leu Asn Leu Pro Arg Ile Ser Thr Glu Ala Cys Glu Val Asp Gly Phe
385                 390                 395                 400

CAC ATA CCA AAA AAC ACT AGA CTA ATA GTG AAC ATA TGG GCA ATA GGG           1427
His Ile Pro Lys Asn Thr Arg Leu Ile Val Asn Ile Trp Ala Ile Gly
                405                 410                 415

AGG GAC CCT AAA GTG TGG GAA AAT CCA TTA GAT TTT ACT CCG GAA CGT           1475
Arg Asp Pro Lys Val Trp Glu Asn Pro Leu Asp Phe Thr Pro Glu Arg
            420                 425                 430

TTC TTG AGT GAA AAA CAC GCG AAA ATT GAT CCG CGA GGT AAT CAT TTT           1523
Phe Leu Ser Glu Lys His Ala Lys Ile Asp Pro Arg Gly Asn His Phe
                435                 440                 445
```

```
GAG TTA ATC CCA TTT GGG GCT GGA CGA AGG ATA TGT GCA GGG GCT AGA    1571
Glu Leu Ile Pro Phe Gly Ala Gly Arg Arg Ile Cys Ala Gly Ala Arg
    450                 455                 460

ATG GGA GCG GCC TCG GTC GAG TAC ATA TTA GGT ACA TTG GTG CAC TCA    1619
Met Gly Ala Ala Ser Val Glu Tyr Ile Leu Gly Thr Leu Val His Ser
465                 470                 475                 480

TTT GAT TGG AAA TTG CCT GAT GGA GTT GTG GAA GTT AAT ATG GAA GAG    1667
Phe Asp Trp Lys Leu Pro Asp Gly Val Val Glu Val Asn Met Glu Glu
                485                 490                 495

AGC TTT GGG ATC GCA TTG CAA AAA AAA GTG CCT CTT TCT GCT ATT GTT    1715
Ser Phe Gly Ile Ala Leu Gln Lys Lys Val Pro Leu Ser Ala Ile Val
                500                 505                 510

ACT CCA AGA TTG CCT CCA AGT TCT TAC ACT GTC TAGGCAAATG CTTATATATA  1768
Thr Pro Arg Leu Pro Pro Ser Ser Tyr Thr Val
                515                 520

TGAATAATTG ATTGAGTTGT TTAGTTGTAT GAAAGATTTG AGAAAATAAA TTATTAGGTT  1828

TTGCACCATT ATGTTGAGAT GGTTGTTGTT AGTGTTAAGG AAGTCGATTG TAGTAATAAT  1888

AATTTTATTT TTTTCGAAAA AAAAAAAAAA AAAAAAAA                          1927

(2) INFORMATION FOR SEQ ID NO:65:

(i) SEQUENCE CHARACTERISTICS:
        (A) LENGTH: 506 amino acids
        (B) TYPE: amino acid
        (C) STRANDEDNESS: single
        (D) TOPOLOGY: linear (ii) MOLECULE TYPE:peptide (vi) ORIGINAL SOURCE:
        (A) ORGANISM: Petunia hybrida
        (B) STRAIN: Falcon Blue (ix) FEATURE:
        (A) NAME/KEY: CDS
        (B) LOCATION: 116 to 1633
        (C) IDENTIFICATION METHOD:by experiment (xi) SEQUENCE DESCRIPTION: SEQ ID NO:65:
```

```
                                                            Met
                                                             1

Met Leu Leu Thr Glu Leu Gly Ala Ala Thr Ser Ile Phe Leu Ile Ala
        5                   10                  15

His Ile Ile Ser Thr Leu Ile Ser Lys Thr Thr Gly Arg His Leu
    20                  25                  30

Pro Pro Gly Pro Arg Gly Trp Pro Val Ile Gly Ala Leu Pro Leu Leu
35                  40                  45

Gly Ala Met Pro His Val Ser Leu Ala Lys Met Ala Lys Tyr Gly
50                  55                  60                  65

Ala Ile Met Tyr Leu Lys Val Gly Thr Cys Gly Met Ala Val Ala Ser
            70                  75                  80

Thr Pro Asp Ala Ala Lys Ala Phe Leu Lys Thr Leu Asp Ile Asn Phe
                85                  90                  95

Ser Asn Arg Pro Pro Asn Ala Gly Ala Thr His Leu Ala Tyr Asn Ala
            100                 105                 110

Gln Asp Met Val Phe Ala His Tyr Gly Pro Arg Trp Lys Leu Leu Arg
        115                 120                 125

Lys Leu Ser Asn Leu His Met Leu Gly Gly Lys Ala Leu Glu Asn Trp
130                 135                 140                 145

Ala Asn Val Arg Ala Asn Glu Leu Gly His Met Leu Lys Ser Met Ser
```

```
                    150                 155                 160
Asp Met Ser Arg Glu Gly Gln Arg Val Val Ala Glu Met Leu Thr
                165                 170                 175
Phe Ala Met Ala Asn Met Ile Gly Gln Val Met Leu Ser Lys Arg Val
            180                 185                 190
Phe Val Asp Lys Gly Val Glu Val Asn Glu Phe Lys Asp Met Val Val
        195                 200                 205
Glu Leu Met Thr Ile Ala Gly Tyr Phe Asn Ile Gly Asp Phe Ile Pro
210                 215                 220                 225
Cys Leu Ala Trp Met Asp Leu Gln Gly Ile Glu Lys Arg Met Lys Arg
                230                 235                 240
Leu His Lys Lys Phe Asp Ala Leu Leu Thr Lys Met Phe Asp Glu His
                245                 250                 255
Lys Ala Thr Thr Tyr Glu Arg Lys Gly Lys Pro Asp Phe Leu Asp Val
            260                 265                 270
Val Met Glu Asn Gly Asp Asn Ser Glu Gly Glu Arg Leu Ser Thr Thr
        275                 280                 285
Asn Ile Lys Ala Leu Leu Leu Asn Leu Phe Thr Ala Gly Thr Asp Thr
290                 295                 300                 305
Ser Ser Ser Ala Ile Glu Trp Ala Leu Ala Glu Met Met Lys Asn Pro
                310                 315                 320
Ala Ile Leu Lys Lys Ala Gln Ala Glu Met Asp Gln Val Ile Gly Arg
                325                 330                 335
Asn Arg Arg Leu Leu Glu Ser Asp Ile Pro Asn Leu Pro Tyr Leu Arg
                340                 345                 350
Ala Ile Cys Lys Glu Thr Phe Arg Lys His Pro Ser Thr Pro Leu Asn
                355                 360                 365
Leu Pro Arg Ile Ser Asn Glu Pro Cys Ile Val Asp Gly Tyr Tyr Ile
370                 375                 380                 385
Pro Lys Asn Thr Arg Leu Ser Val Asn Ile Trp Ala Ile Gly Arg Asp
                390                 395                 400
Pro Gln Val Trp Glu Asn Pro Leu Glu Phe Asn Pro Glu Arg Phe Leu
                405                 410                 415
Ser Gly Arg Asn Ser Lys Ile Asp Pro Arg Gly Asn Asp Phe Glu Leu
                420                 425                 430
Ile Pro Phe Gly Ala Gly Arg Arg Ile Cys Ala Gly Thr Arg Met Gly
435                 440                 445
Ile Val Met Val Glu Tyr Ile Leu Gly Thr Leu Val His Ser Phe Asp
450                 455                 460                 465
Trp Lys Leu Pro Ser Glu Val Ile Glu Leu Asn Met Glu Glu Ala Phe
                470                 475                 480
Gly Leu Ala Leu Gln Lys Ala Val Pro Leu Glu Ala Met Val Thr Pro
                485                 490                 495
Arg Leu Gln Leu Asp Val Tyr Val Pro
                500                 505

(2) INFORMATION FOR SEQ ID NO:66:

(i) SEQUENCE CHARACTERISTICS:
        (A) LENGTH: 510 amino acids
        (B) TYPE: amino acid
        (C) STRANDEDNESS: single
        (D) TOPOLOGY: linear (ii) MOLECULE TYPE:peptide
```

(vi) ORIGINAL SOURCE:
    (A) ORGANISM: Eustoma russellianum (ix) FEATURE:
    (A) NAME/KEY: CDS
    (B) LOCATION: 92 to 1621
    (C) IDENTIFICATION METHOD: by experiment (xi) SEQUENCE DESCRIPTION: SEQ ID NO:66:

```
                              Met Ala Val Gly Asn Gly Val
                                1               5

Leu Leu His Ile Ala Ala Ser Leu Met Leu Phe Phe His Val Gln Lys
            10                  15                  20

Leu Val Gln Tyr Leu Trp Met Asn Ser Arg Arg His Arg Leu Pro Pro
        25                  30                  35

Gly Pro Ile Gly Trp Pro Val Leu Gly Ala Leu Arg Leu Leu Gly Thr
40                  45                  50                  55

Met Pro His Val Ala Leu Ala Asn Met Ala Lys Lys Tyr Gly Pro Val
                60                  65                  70

Met Tyr Leu Lys Val Gly Ser Cys Gly Leu Ala Val Ala Ser Thr Pro
            75                  80                  85

Glu Ala Ala Lys Ala Phe Leu Lys Thr Leu Asp Met Asn Phe Ser Asn
        90                  95                  100

Arg Pro Pro Asn Ala Gly Ala Thr His Leu Ala Tyr Asn Ala Gln Asp
    105                 110                 115

Met Val Phe Ala Asp Tyr Gly Pro Arg Trp Lys Leu Leu Arg Lys Leu
120                 125                 130                 135

Ser Asn Ile His Ile Leu Gly Gly Lys Ala Leu Gln Gly Trp Glu Glu
                140                 145                 150

Val Arg Lys Lys Glu Leu Gly Tyr Met Leu Tyr Ala Met Ala Glu Ser
            155                 160                 165

Gly Arg His Gly Gln Pro Val Val Val Ser Glu Met Leu Thr Tyr Ala
            170                 175                 180

Met Ala Asn Met Leu Gly Gln Val Met Leu Ser Lys Arg Val Phe Gly
185                 190                 195

Ser Gln Gly Ser Glu Ser Asn Glu Phe Lys Asp Met Val Val Glu Leu
200                 205                 210                 215

Met Thr Val Ala Gly Tyr Phe Asn Ile Gly Asp Phe Ile Pro Ser Ile
                220                 225                 230

Ala Trp Met Asp Leu Gln Gly Ile Gln Gly Met Lys Arg Leu His
                235                 240                 245

Lys Lys Phe Asp Ala Leu Leu Thr Arg Leu Leu Glu Glu His Thr Ala
        250                 255                 260

Ser Ala His Glu Arg Lys Gly Ser Pro Asp Phe Leu Asp Phe Val Val
    265                 270                 275

Ala Asn Gly Asp Asn Ser Glu Gly Glu Arg Leu Gln Thr Val Asn Ile
280                 285                 290                 295

Lys Ala Leu Leu Leu Asn Met Phe Thr Ala Gly Thr Asp Thr Ser Ser
                300                 305                 310

Ser Val Ile Glu Trp Ala Leu Ala Glu Leu Leu Lys Asn Pro Ile Ile
            315                 320                 325

Leu Arg Arg Ala Gln Glu Glu Met Asp Gly Val Ile Gly Arg Asp Arg
    330                 335                 340

Arg Phe Leu Glu Ala Asp Ile Ser Lys Leu Pro Tyr Leu Gln Ala Ile
345                 350                 355
```

```
Cys Lys Glu Ala Phe Arg Lys His Pro Ser Thr Pro Leu Asn Leu Pro
360                 365                 370                 375

Arg Ile Ala Ser Gln Ala Cys Glu Val Asn Gly His Tyr Ile Pro Lys
                380                 385                 390

Gly Thr Arg Leu Ser Val Asn Ile Trp Ala Ile Gly Arg Asp Pro Ser
            395                 400                 405

Val Trp Glu Asn Pro Asn Glu Phe Asn Pro Asp Arg Phe Leu Glu Arg
        410                 415                 420

Lys Asn Ala Lys Ile Asp Pro Arg Gly Asn Asp Phe Glu Leu Ile Pro
    425                 430                 435

Phe Gly Ala Gly Arg Arg Ile Cys Ala Gly Thr Arg Leu Gly Ile Leu
440                 445                 450                 455

Leu Val Glu Tyr Ile Leu Gly Thr Leu Val His Ser Phe Val Trp Glu
                460                 465                 470

Leu Pro Ser Ser Val Ile Glu Leu Asn Met Asp Glu Ser Phe Gly Leu
            475                 480                 485

Ala Leu Gln Lys Ala Val Pro Leu Ala Ala Met Val Thr Pro Arg Leu
        490                 495                 500

Pro Leu His Ile Tyr Ser Pro
    505                 510
```

(2) INFORMATION FOR SEQ ID NO:67:

(i) SEQUENCE CHARACTERISTICS:
       (A) LENGTH: 523 amino acids
       (B) TYPE: amino acid
       (C) STRANDEDNESS: single
       (D) TOPOLOGY: linear (ii) MOLECULE TYPE:peptide (vi) ORIGINAL SOURCE:
       (A) ORGANISM: Campanula medium (ix) FEATURE:
       (A) NAME/KEY: CDS
       (B) LOCATION: 180 to 1748
       (C) IDENTIFICATION METHOD:by experiment (xi) SEQUENCE DESCRIPTION: SEQ ID NO:67:

```
Met Ser Ile Asp Ile Ser Thr Leu Phe Tyr Glu Leu Val Ala Ala Ile
1               5                   10                  15

Ser Leu Tyr Leu Ala Thr Tyr Ser Phe Ile Arg Phe Leu Phe Lys Pro
                20                  25                  30

Ser His His His His Leu Pro Pro Gly Pro Thr Gly Trp Pro Ile Ile
            35                  40                  45

Gly Ala Leu Pro Leu Leu Gly Thr Met Pro His Val Ser Leu Ala Asp
50                  55                  60

Met Ala Val Lys Tyr Gly Pro Ile Met Tyr Leu Lys Leu Gly Ser Lys
65                  70                  75                  80

Gly Thr Val Val Ala Ser Asn Pro Lys Ala Ala Arg Ala Phe Leu Lys
                85                  90                  95

Thr His Asp Ala Asn Phe Ser Asn Arg Pro Ile Asp Gly Gly Pro Thr
            100                 105                 110

Tyr Leu Ala Tyr Asn Ala Gln Asp Met Val Phe Ala Glu Tyr Gly Pro
        115                 120                 125

Lys Trp Lys Leu Leu Arg Lys Leu Cys Ser Leu His Met Leu Gly Pro
    130                 135                 140

Lys Ala Leu Glu Asp Trp Ala His Val Lys Val Ser Glu Val Gly His
```

-continued

```
145                 150                 155                 160
Met Leu Lys Glu Met Tyr Glu Gln Ser Ser Lys Ser Val Pro Val Pro
                165                 170                 175

Val Val Val Pro Glu Met Leu Thr Tyr Ala Met Ala Asn Met Ile Gly
            180                 185                 190

Arg Ile Ile Leu Ser Arg Arg Pro Phe Val Ile Thr Ser Lys Leu Asp
        195                 200                 205

Ser Ser Ala Ser Ala Ser Ala Ser Val Ser Glu Phe Gln Tyr Met Val
    210                 215                 220

Met Glu Leu Met Arg Met Ala Gly Leu Phe Asn Ile Gly Asp Phe Ile
225                 230                 235                 240

Pro Tyr Ile Ala Trp Met Asp Leu Gln Gly Ile Gln Arg Asp Met Lys
            245                 250                 255

Val Ile Gln Lys Lys Phe Asp Val Leu Leu Asn Lys Met Ile Lys Glu
        260                 265                 270

His Thr Glu Ser Ala His Asp Arg Lys Asp Asn Pro Asp Phe Leu Asp
    275                 280                 285

Ile Leu Met Ala Ala Thr Gln Glu Asn Thr Glu Gly Ile Gln Leu Asn
    290                 295                 300

Leu Val Asn Val Lys Ala Leu Leu Leu Asp Leu Phe Thr Ala Gly Thr
305                 310                 315                 320

Asp Thr Ser Ser Val Ile Glu Trp Ala Leu Ala Glu Met Leu Asn
            325                 330                 335

His Arg Gln Ile Leu Asn Arg Ala His Glu Glu Met Asp Gln Val Ile
            340                 345                 350

Gly Arg Asn Arg Arg Leu Glu Gln Ser Asp Ile Pro Asn Leu Pro Tyr
        355                 360                 365

Phe Gln Ala Ile Cys Lys Glu Thr Phe Arg Lys His Pro Ser Thr Pro
    370                 375                 380

Leu Asn Leu Pro Arg Ile Ser Thr Glu Ala Cys Glu Val Asp Gly Phe
385                 390                 395                 400

His Ile Pro Lys Asn Thr Arg Leu Ile Val Asn Ile Trp Ala Ile Gly
            405                 410                 415

Arg Asp Pro Lys Val Trp Glu Asn Pro Leu Asp Phe Thr Pro Glu Arg
            420                 425                 430

Phe Leu Ser Glu Lys His Ala Lys Ile Asp Pro Arg Gly Asn His Phe
        435                 440                 445

Glu Leu Ile Pro Phe Gly Ala Gly Arg Arg Ile Cys Ala Gly Ala Arg
    450                 455                 460

Met Gly Ala Ala Ser Val Glu Tyr Ile Leu Gly Thr Leu Val His Ser
465                 470                 475                 480

Phe Asp Trp Lys Leu Pro Asp Gly Val Val Glu Val Asn Met Glu Glu
            485                 490                 495

Ser Phe Gly Ile Ala Leu Gln Lys Lys Val Pro Leu Ser Ala Ile Val
        500                 505                 510

Thr Pro Arg Leu Pro Pro Ser Ser Tyr Thr Val
            515                 520
```